United States Patent [19]

Morriello et al.

[11] Patent Number: 5,494,919
[45] Date of Patent: Feb. 27, 1996

[54] 2-SUBSTITUTED PIPERIDINES, PYRROLIDINES AND HEXAHYDRO-1H-AZEPINES PROMOTE RELEASE OF GROWTH HORMONE

[75] Inventors: Gregori J. Morriello, Belleville; Arthur A. Patchett, Westfield; Lihu Yang, Edison, all of N.J.

[73] Assignee: Merck & Co., Inc., Rahway, N.J.

[21] Appl. No.: 323,994

[22] Filed: Oct. 17, 1994

Related U.S. Application Data

[63] Continuation-in-part of Ser. No. 149,441, Nov. 9, 1993, abandoned.

[51] Int. Cl.⁶ .................. A61K 31/445; C07D 401/06; C07D 209/04
[52] U.S. Cl. .......................... 514/323; 514/318; 514/319; 514/322; 514/324; 514/326; 514/362; 514/363; 514/365; 514/372; 514/394; 514/396; 514/414; 544/335; 546/193; 546/199; 546/201; 546/202; 546/205; 546/209; 546/210; 548/127; 548/128; 548/205; 548/214; 548/253; 548/306.1; 548/467; 548/468
[58] Field of Search ................ 544/335; 546/193, 546/199, 201, 202, 205, 209, 210; 548/127, 128, 205, 214, 253, 306.1, 467, 468; 514/318, 319, 322, 323, 324, 326, 362, 363, 365, 372, 394, 396, 414

[56] References Cited

U.S. PATENT DOCUMENTS

| | | | |
|---|---|---|---|
| 3,239,345 | 3/1966 | Hodge et al. | 514/450 |
| 4,036,979 | 7/1977 | Asato | 514/443 |
| 4,299,821 | 11/1981 | Kisfaludy et al. | 514/17 |
| 4,411,890 | 10/1983 | Momany | 514/17 |
| 4,782,139 | 11/1988 | DiMarchi | 530/407 |
| 5,137,872 | 8/1992 | Seely | 514/12 |
| 5,164,368 | 11/1992 | Recker | 514/12 |
| 5,206,235 | 4/1993 | Fisher et al. | 514/213 |
| 5,283,241 | 2/1994 | Bochis et al. | 514/183 |
| 5,284,841 | 2/1994 | Chu et al. | 514/183 |
| 5,310,737 | 5/1994 | Fisher et al. | 514/215 |
| 5,317,017 | 5/1994 | Ok et al. | 514/211 |

FOREIGN PATENT DOCUMENTS

| | | |
|---|---|---|
| 0144230A3 | 6/1985 | European Pat. Off. . |
| WO94/07486 | 4/1994 | WIPO . |
| WO94/08583 | 4/1994 | WIPO . |
| WO94/13696 | 6/1994 | WIPO . |
| WO94/19367 | 9/1994 | WIPO . |

OTHER PUBLICATIONS

Ammana et al "IGF–I and pamidronate increase bone mineral density in ovarietomized rat" Am. J. Physiology 265 pp. E770–E776 (1993).

R. G. Smith, et al., *Science*, Reprint Series, 11 Jun. 1993, vol. 260, pp. 1640–1643 "A Nonpeptidyl Growth Hormone Secretagogue".

Primary Examiner—Ceila Chang
Attorney, Agent, or Firm—J. Eric Thies; David L. Rose

[57] ABSTRACT

The present invention is directed to certain piperidine, pyrrolidine, and hexahydro-1H-azepine compounds of the general structural formula:

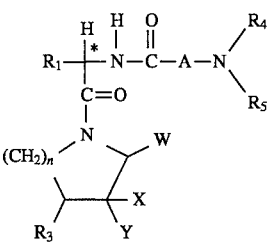

wherein $R_1$, $R_3$, $R_4$, $R_5$, A, W, X, Y, and n axe as defined herein. These compounds promote the release of growth hormone in humans and animals. This property can be utilized to promote the growth of food animals to render the production of edible meat products more efficient, and in humans, to treat physiological or medical conditions characterized by a deficiency in growth hormone secretion, such as short stature in growth hormone deficient children, and to treat medical conditions which s are improved by the anabolic effects of growth hormone. Growth hormone releasing compositions containing such compounds as the active ingredient thereof are also disclosed.

7 Claims, No Drawings

2-SUBSTITUTED PIPERIDINES, PYRROLIDINES AND HEXAHYDRO-1H-AZEPINES PROMOTE RELEASE OF GROWTH HORMONE

CROSS REFERENCE TO RELATED APPLICATIONS

This application is a continuation-in-part of application Ser. No. 08/149,441, filed Nov. 9, 1993, now abandoned.

BACKGROUND OF THE INVENTION

Growth hormone, which is secreted from the pituitary, stimulates growth of all tissues of the body that are capable of growing. In addition, growth hormone is known to have the following basic effects on the metabolic processes of the body:

1. Increased rate of protein synthesis in all cells of the body;
2. Decreased rate of carbohydrate utilization in cells of the body;
3. Increased mobilization of free fatty acids and use of fatty acids for energy.

A deficiency in growth hornhone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering GRF or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recently, recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. Non peptidal growth hormone secretagogues with a benzo-lactam structure are disclosed in U.S. Pat. No. 4,206,235. The instant compounds are low molecular weight peptide analogs for promoting the release of growth hormone which have good stability in a variety of physiological environments and which may be administered parenterally, nasally or by the oral route.

SUMMARY OF THE INVENTION

The instant invention is directed to certain 2-substituted piperidine, pyrrolidine, and hexahydro-1H-azepine compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the 2-substituted piperidine, pyrrolidine, and hexahydro-1H-azepine compounds. It is a further object of this invention to describe procedures for the preparation of such compounds. A still further object is to describe the use of such compounds to increase the secretion of growth hormone in humans and animals. A still further object of this invention is to describe compositions containing the 2-substituted pipeddine, pyrrolidine, and hexahydro-1H-azepine compounds for the use of treating humans and animals so as to increase the level of growth hormone secretions. Further objects will become apparent from a reading of the following description.

DESCRIPTION OF THE INVENTION

The novel 2-substituted piperdine, pyrrolidine, and hexahydro-1H-azepine compounds of the instant invention are best described in the following structural formula I:

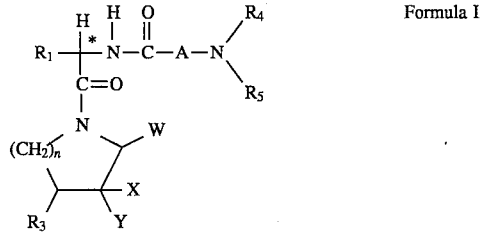

Formula I wherein:

$R_1$ is selected from the group consisting of: $C_1$–$C_{10}$ alkyl, aryl, aryl($C_1$–$C_6$ alkyl), ($C_3$–$C_7$ cycloalkyl)($C_1$–$C_6$ alkyl)—, ($C_1$–$C_5$ alkyl)-K-($C_1$–$C_5$ alkyl)—, aryl($C_0$–$C_5$ alkyl)-K-($C_1$–$C_5$ alkyl)—, and ($C_3$–$C_7$ cycloalkyl)($C_0$–$C_5$ alkyl)-K-($C_1$–$C_5$ alkyl)—, where K is O, $S(O)_m$, $N(R_2)C(O)$, $C(O)N(R_2)$, $OC(O)$, $C(O)O$, —$CR_2$=$CR_2$—, or —C≡C—, where aryl is selected from: phenyl, naphthyl, indolyl, azaindole, pyridyl, benzothienyl, benzofuranyl, thiazolyl, and benzimidazolyl, and $R_2$ and alkyl may be further substituted by 1 to 9 halogen, $S(O)_m R_{2a}$, 1 to 3 of $OR_{2a}$ or $C(O)OR_{2a}$, and aryl may be further substituted by 1 to 3 of $C_1$–$C_6$ alkyl, 1 to 3 of halogen, 1 to 2 of $OR_2$, methylenedioxy, —$S(O)_m R_2$, 1 to 2 of —$CF_3$, —$OCF_3$, nitro, —$N(R_2)C(O)(R_2)$, —$C(O)OR_2$, —$C(O)N(R_2)(R_2)$, -1H-tetrazol-5-yl, —$SO_2N(R_2)(R_2)$, —$N(R_2)SO_2$ phenyl, or —$N(R_2)SO_2R_2$;

$R_2$ is selected from: hydrogen, $C_1$–$C_6$ alkyl, and $C_3$–$C_7$ cycloalkyl, and where two $C_1$–$C_6$ alkyl groups are present on one atom, they may be optionally joined to form a $C_3$–$C_8$ cyclic ring, optionally including oxygen, sulfur or $NR_{3a}$;

$R_3$ is selected from: hydrogen, —$(CH_2)_r$phenyl, —$(CH_2)_r$naphthyl, —$C_1$–$C_{10}$ alkyl, —$C_3$–$C_7$ cycloalkyl, where the phenyl, naphthyl and $C_3$–$C_7$ cycloalkyl rings may be substituted by 1 to 3 substituents selected from the group consisting of: $C_1$–$C_6$ alkyl, halogen, —$OR_2$, —$NHSO_2CF_3$, —$(CH_2)_rOR_6$, —$(CH_2)_rN(R_2)(R_6)$, —$(CH_2)_r(R_6)$, —$(CH_2)_rC(O)OR_2$, —$(CH_2)_rC(O)OR_6$, —$(CH_2)_rOC(O)R_2$, —$(CH_2)_rOC(O)R_6$, —$(CH_2)_rC(O)R_2$, —$(CH_2)_rC(O)R_6$, —$(CH_2)_rC(O)N(R_2)(R_2)$, —$(CH_2)_rC(O)N(R_2)(R_6)$, —$(CH_2)_rN(R_2)C(O)R_2$, —$(CH_2)_rN(R_2)C(O)R_6$, —$(CH_2)_rN(R_6)C(O)R_2$, —$(CH_2)_rN(R_6)C(O)R_6$, —$(CH_2)_rN(R_2)C(O)OR_2$, —$(CH_2)_rN(R_2)C(O)OR_6$, —$(CH_2)_rN(R_6)C(O)OR_2$, —$(CH_2)_rN(R_6)C(O)OR_6$, —$(CH_2)_rN(R_2)C(O)N(R_2)(R_6)$, —$(CH_2)_rN(R_2)C(O)N(R_2)(R_2)$, —$(CH_2)_rN(R_6)C(O)N(R_2)(R_6)$, $(CH_2)_rN(R_2)SO_2R_6$, —$(CH_2)_rN(R_2)SO_2R_2$, —$(CH_2)_rN(R_6)SO_2R_2$, $CH_2)_rN(R_6)SO_2R_6$, —$(CH_2)_rOC(O)N(R_2)(R_6)$, —$(CH_2)_rOC(O)N(R_2)(R_2)$, —$(CH_2)_rSO_2N(R_2)(R_6)$, —$(CH_2)_rSO_2N(R_2)(R_2)$, $(CH_2)_rSO_2NHC(O)R_6$, $(CH_2)_rSO_2NHC(O)R_2$, —$(CH_2)_rSO_2NHC(O)OR_6$, —$(CH_2)_rSO_2NHC(O)OR_2$, —$(CH_2)_rC(O)NHC(O)NR_2$, —$(CH_2)_rC(O)NHC(O)NR_6$, —$(CH_2)_rC(O)NHC(O)R_2$, —$(CH_2)_rCONHC(O)R_6$, —$(CH_2)_rCONHSO_2R_6$, —$(CH_2)_rCONHSO_2R_2$, —$(CH_2)_rCONHSO_2N(R_2)R_2$, —$(CH_2)_rCONHSO_2N(R_2)R_6$, —$(CH_2)_rN(R_2)SO_2N(R_2)R_6$, —$(CH_2)_rN(R_6)SO_2N(R_2)R_6$, —$(CH_2)_rS(O)_mR_6$, and —$(CH_2)_rS(O)_mR_2$;

$R_{3a}$ is hydrogen, $C_1$–$C_6$ alkyl optionally substituted by hydroxyl;

W is selected from the group consisting of: —CN, —$C(O)R_8$, —$C(O)R_2$, —$C(O)O(CH_2)_1$aryl, —$C(O)N(R_2)(R_2)$; —$C(O)N(R_2)(R_8)$, —$C(O)N(R_2)(CH_2)_1$aryl, —$CH_2N(R_2)C(O)R_8$, —$CH_2N(R_2)C(O)(CH_2)_1$aryl, —$(CH_2)_rOR_2$, —$CH(OH)R_2$, —$CH(OH)(CH_2)_1$aryl, —$C(O)R_2$, —$C(O)(CH_2)_1$aryl, 1H-tetrazol-5-yl, 5-amino-1, 2,4-oxadiazol-3-yl, and 5-methyl-1, 2, 4-oxadiazol-3-yl, where $R_8$ is hydrogen, $C_1$–$C_6$ alkyl, or $C_1$–$C_6$ alkyl substituted by $OR_2$, $C(O)OR_2$, $CON(R_2)(R_2)$, $N(R_2)C(O)R_2$, $N(R_2)C(O)N(R_2)(R_2)$, and aryl is phenyl, pyridyl, or 1H-tetrazol-5yl;

X is selected from: hydrogen, —C≡N, —$(CH_2)_qN(R_2)C(O)R_2$, —$(CH_2)_qN(R_2)C(O)(CH_2)_t$aryl, —$(CH_2)_qN(R_2)SO_2(CH_2)_t$aryl, —$(CH_2)_qN(R_2)SO_2R_2$, —$(CH_2)_qN(R_2)C(O)N(R_2)(CH_2)_t$aryl, —$(CH_2)_qN(R_2)C(O)N(R_2)(R_2)$, —$(CH_2)_qC(O)N(R_2)(R_2)$, —$(CH_2)_qC(O)N(R_2)(CH_2)_t$aryl, —$(CH_2)_qC(O)OR_2$, —$(CH_2)_qC(O)O(CH_2)_t$aryl, —$(CH_2)_qOR_2$, —$(CH_2)_qOC(O)R_2$, —$(CH_2)_qOC(O)(CH_2)_t$aryl, —$(CH_2)_qOC(O)N(R_2)(CH_2)_t$aryl, —$(CH_2)_qOC(O)N(R_2)(R_2)$, —$(CH_2)_qC(O)R_2$, —$(CH_2)_qC(O)(CH_2)_t$ aryl, —$(CH_2)_qN(R_2)C(O)OR_2$, —$(CH_2)_qN(R_2)SO_2N(R_2)(R_2)$, —$(CH_2)_qS(O)_mR_2$, and —$(CH_2)_qS(O)_m(CH_2)_t$aryl, where an $R_2$, $(CH_2)_q$ and $(CH_2)_t$ group may be optionally substituted by 1 to 2 $C_1$–$C_4$ alkyl, hydroxyl, $C_1$–$C_4$ lower alkoxy, carboxyl, $CONH_2$, $S(O)_mCH_3$, carboxylate $C_1$–$C_4$ alkyl esters, or 1H-tetrazol-5-yl, and aryl is phenyl, naphthyl, pyridyl, thiazolyl, or 1H-tetrazol-5-yl groups which may be optionally substituted by 1 to 3 halogen, 1 to 3 —$OR_2$, —$CON(R_2)(R_2)$, —$C(O)OR_2$, 1 to 3 $C_1$–$C_4$ alkyl, —$S(O)_mR_2$, or 1H-tetrazol-5-yl;

Y is selected from: hydrogen, $C_1$–$C_{10}$ alkyl, —$(CH_2)_t$aryl, —$(CH_2)_q(C_3$–$C_7$ cycloalkyl), —$(CH_2)_q$-K-$(C_1$–$C_6$ alkyl), —$(CH_2)_q$-K-$(CH_2)_t$aryl, —$(CH_2)_q$-K-$(CH_2)_t(C_3$–$C_7$ cycloalkyl containing O, $NR_2$, S), and —$(CH_2)_q$-K-$(CH_2)_t(C_3$–$C_7$ cycloalkyl), where K is O, $S(O)_m$, $C(O)NR_2$, CH=CH, C≡C, $N(R_2)C(O)$, $C(O)NR_2$, C(O)O, or OC(O), and where the alkyl, $R_2$, $(CH_2)_q$ and $(CH_2)_t$ groups may be optionally substituted by $C_1$–$C_4$ alkyl, hydroxyl, $C_1$–$C_4$ lower alkoxy, carboxyl, —$CONH_2$ or carboxylate $C_1$–$C_4$ alkyl esters, and aryl is phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrrazinyl, or isothiazolyl which is optionally substituted by 1 to 3 halogen, 1 to 3 —$OR_2$,—$C(O)OR_2$,—$C(O)N(R_2)(R_2)$, nitro, cyano, benzyl, 1 to 3 $C_1$–$C_4$ alkyl, —$S(O)_mR_2$, or 1H-tetrazol-5-yl;

$R_4$ and $R_5$ are independently hydrogen, $C_1$–$C_6$ alkyl, substituted $C_1$–$C_6$ alkyl where the substituents may be 1 to 5 halo, 1 to 3 hydroxy, 1 to 3 $C_1$–$C_{10}$ alkanoyloxy, 1 to 3 $C_1$–$C_6$ alkoxy, phenyl, phenoxy, 2-furyl, $C_1$–$C_6$ alkoxycarbonyl, $S(O)_m(C_1$–$C_6$ alkyl); or $R_4$ and $R_5$ can be taken together to form —$(CH_2)_dL_a(CH_2)_e$- where $L_a$ is $C(R_2)_2$, O, $S(O)_m$ or $N(R_2)$, d and e are independently 1 to 3 and $R_2$ is as defined above;

A is:

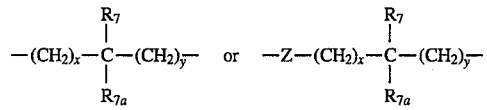

where x and y are independently 0, 1, 2 or 3;

Z is N-$R_{6a}$ or O, where $R_{6a}$ is hydrogen or $C_1$–$C_6$ alkyl;

$R_6$ is hydrogen, $C_1$–$C_6$ alkyl, or $(CH_2)_v$aryl, wherein the alkyl and $(CH_2)_v$ groups may be optionally substituted by 1-2O($R_2$), $S(O)_mR_2$, 1H-tetrazol-5-yl, $C(O)OR_2$, $C(O)N(R_2)(R_2)$ or $SO_2N(R_2)(R_2)$, $N(R_2)C(O)N(R_2)(R_2)$, and wherein aryl is phenyl, pyridyl, 1H-tetrazol-5-yl, triazolyl, imidazolyl, thiazolyl, pyrazolyl, thiadiazolyl, imidazolone-1-yl, benzimidazol-2-yl, triazolinone-yl optionally substituted with $C_1$–$C_6$ alkyl, $C_3$–$C_6$ cycloalkyl, amino, or hydroxyl;

$R_7$ and $R_{7a}$ are independently hydrogen, $C_1$–$C_6$ alkyl, trifluoromethyl, phenyl, substituted $C_1$–$C_6$ alkyl where the substituents are imidazolyl, phenyl, indolyl, p-hydroxyphenyl, $OR_2$, $S(O)_mR_2$, $C(O)O(C_1$–$C_6$ alkyl), $C_3$–$C_7$ cycloalkyl, $N(R_2)(R_2)$, $C(O)N(R_2)(R_2)$; or $R_7$ and $R_{7a}$ can independently be joined to one or both of $R_4$ and $R_5$ groups to form alkylene bridges between the terminal nitrogen and the alkyl portion of the $R_7$ or $R_{7a}$ groups, wherein the bridge contains 1 to 5 carbons atoms; or $R_7$ and $R_{7a}$ can be joined to one another to form a $C_3$–$C_7$ cycloalkyl;

l is 0, 1 or 2;
m is 0, 1, or 2;
n is 1, 2, or 3;
q is 0, 1, 2, 3, or 4;
r is 0, 1, or 2, or 3;
t is 0, 1, 2, or 3;
v is 0, 1, or 2;

and pharmaceutically acceptable salts and individual diastereomers thereof.

When n is 1, a pyrrolidine ring is formed, when n is 2 a piperidine ring is formed and when n is 3 the ring is designated as a hexahydro- 1H-azepine.

In the above structural formula and throughout the instant specification, the following terms have the indicated meanings:

The alkyl groups specified above are intended to include those alkyl groups of the designated length in either a straight or branched configuration which may optionally contain double or triple bonds. Exemplary of such alkyl groups are methyl, ethyl, propyl, isopropyl, butyl, sec-butyl, tertiary butyl, pentyl, isopentyl, hexyl, isohexyl, allyl, propinyl, butadienyl, hexenyl and the like.

The alkoxy groups specified above are intended to include those alkoxy groups of the designated length in either a straight or branched configuration which may optionally contain double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, propinyloxy, isobutenyloxy, hexenyloxy and the like.

The term "halogen" is intended to include the halogen atom fluorine, chlorine, bromine and iodine.

The term "aryl" within the present invention, unless otherwise specified, is intended to include aromatic rings, such as carbocyclic and heterocyclic aromatic rings selected the group consisting of: phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrrazinyl, or isothiazolyl, which may be optionally substituted by 1 to 3 of $C_1$–$C_6$ alkyl, 1 to 3 of halogen, 1 to 2 of $OR_2$, methylenedioxy, —$S(O)_m R_2$, 1 to 2 of —$CF_3$, —$OCF_3$, nitro, —$N(R_2)C(O)(R_2)$, —$C(O)OR_2$, —$C(O)N(R_2)(R_2)$, -1H-tetrazol-5-yl, —$SO_2N(R_2)(R_2)$, —$N(R_2)SO_2$ phenyl, or —$N(R_2)SO_2R_2$, wherein $R_2$ is as defined herein.

Certain of the above defined terms may occur more than once in the above formula and upon such occurrence each term shall be defined independently of the other.

Preferred compounds of the instant invention include those of Formula Ia:

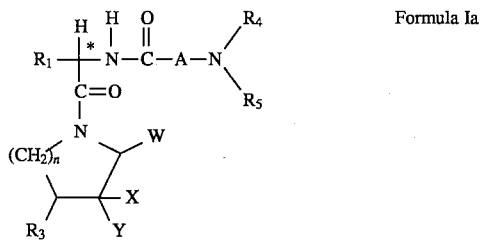

Formula Ia wherein:

$R_1$ is selected from the group consisting of: $C_1$–$C_{10}$ alkyl, aryl ($C_1$–$C_4$ alkyl)-, $C_3$–$C_6$ cycloalkyl ($C_1$–$C_4$ alkyl)-, ($C_1$–$C_4$ alkyl)-K-($C_1$–$C_2$ alkyl)-, aryl ($C_0$–$C_2$ alkyl)-K-($C_1$–$C_2$ alkyl)-, and ($C_3$–$C_7$ cycloalkyl)($C_0$–$C_2$ alkyl)-K-($C_1$–$C_2$ alkyl)-, where K is O, $S(O)_m$, OC(O), C(O)O and the alkyl groups may be further substituted by 1 to 7 halogen, $S(O)_m R_2$, 1 to 3 $OR_2$ or $C(O)OR_2$ and aryl is phenyl, naphthyl, indolyl, pyridyl, benzothienyl, or benzofuranyl which may be further substituted by 1–2 $C_1$–$C_4$ alkyl, 1 to 2 halogen, 1 to 2 $OR_2$, $S(O)_m R_2$ or $C(O)OR_2$;

$R_2$ is hydrogen, $C_1$–$C_6$ alkyl, or $C_3$–$C_7$ cycloalkyl and where two $C_1$–$C_6$ alkyl groups are present on one atom they may be optionally joined to form a $C_4$–$C_7$ cyclic ring optionally including oxygen, sulfur or $NR_{3a}$;

$R_3$ is hydrogen or phenyl optionally substituted in the ortho position by a $C_1$–$C_6$ alkyl group, —$NHSO_2CF_3$, —$(CH_2)_r(1H$-tetrazol-5-yl), —$(CH_2)_rC(O)OR_2$, $(CH_2)_rC(O)N(R_2)(R_6)$;

$R_{3a}$ is hydrogen, or $C_1$–$C_4$ alkyl;

W is —CN, —$C(O)OR_2$, —$C(O)N(R_2)(R_2)$, —$C(O)N(R_2)(CH_2)_1$phenyl, 1H-tetrazol-5-yl, or —$(CH_2)_rOR_2$;

X is hydrogen, —$(CH_2)_qC(O)N(R_2)(R_6)$, or —$(CH_2)_qC(O)OR_2$;

Y is hydrogen, $C_1$–$C_8$ alkyl, —$(CH_2)_t$phenyl, —$(CH_2)_t$pyridyl, or —$(CH_2)_t$thiazolyl;

$R_4$ and $R_5$ are independently hydrogen, $C_1$–$C_6$ alkyl, or substituted $C_1$–$C_6$ alkyl where the substituents may be 1 to 5 halo, 1 to 3 hydroxyl, $S(O)m(C_1$–$C_6$ alkyl) or phenyl;

$R_6$ is hydrogen, or $C_1$–$C_6$ alkyl;

A is:

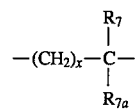

where x is 0, or 1;

$R_7$ and $R_{7a}$ are independently hydrogen $C_1$–$C_6$ alkyl, trifluoromethyl, phenyl, substituted $C_1$–$C_6$ alkyl where the substituents are imidazolyl, phenyl, indolyl, p-hydroxyphenyl, $OR_2$, $S(O)_m R_2$, $C(O)O(C_1$–$C_6$ alkyl), $C_5$–$C_7$ cycloalkyl, $N(R_2)(R_2)$, $C(O)N(R_2)(R_2)$; or $R_7$ and $R_{7a}$ can independently be joined to one of $R_4$ or $R_5$ to form alkylene bridges between the terminal nitrogen and the alkyl portion of $R_7$ or $R_{7a}$ groups to form 5 or 6 membered rings; or $R_7$ and $R_{7a}$ can be joined to one another to form a $C_3$ cycloalkyl;

l is 0 or 1;
n is 2;
m is 0, 1, or 2;
r is 0, 1, 2 or 3;
q is 0 or 1
t is 0 or 1;

and pharmaceutically acceptable salts and individual diastereomers thereof.

More preferred compounds of the instant invention include those of Formula Ib:

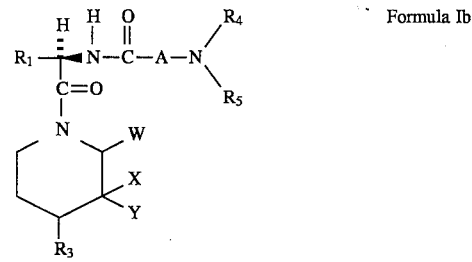

Formula Ib wherein:

$R_1$ is selected from the group consisting of: $C_1$–$C_{10}$ alkyl, aryl ($C_1$–$C_3$ alkyl)-, and aryl ($C_0$–$C_1$ alkyl)-K-($C_1$–$C_2$ alkyl)-, where K is O or $S(O)_m$ and the aryl is phenyl, pyridyl, naphthyl, or indolyl which are optionally substituted by 1–2 $C_1$–$C_4$ alkyl, 1 to 2 halogen, 1 to 2 $OR_2$, $S(O)_m R_2$ or $C(O)OR_2$;

$R_2$ is hydrogen, $C_1$–$C_6$ alkyl, or $C_3$–$C_7$ cycloalkyl and where two $C_1$–$C_6$ alkyl groups are present on one atom they may be optionally joined to form a $C_5$–$C_7$ cyclic ring optionally including oxygen, sulfur or $NR_{3a}$;

$R_3$ is hydrogen or phenyl optionally substituted in the ortho position by a $C_1$–$C_3$ alkyl group, $(CH_2)_r(1H$-tetrazol-5-yl) or $(CH_2)_rC(O)OR_2$;

$R_{3a}$ is hydrogen, or $C_1$–$C_4$ alkyl;

W is —CN, —$C(O)OR_2$, or —$C(O)N(R_2)R_2)$;

X is hydrogen or $C(O)OR_2$;

Y is hydrogen, benzyl, picoyl, or thiazolylmethyl;

$R_4$ and $R_5$ are independently hydrogen, $C_1$–$C_3$ alkyl, substituted $C_1$–$C_3$ alkyl where the substituents may be 1 to 2 hydroxyl;

A is

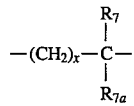

where x is 0, or 1;

$R_7$ and $R_{7a}$ are independently hydrogen or $C_1$–$C_4$ alkyl;

m is 0, 1, or 2;
r is 0, 1, or 2; and pharmaceutically acceptable salts and individual diastereomers thereof.
The most preferred growth hormone releasing compounds of the present invention include the following:
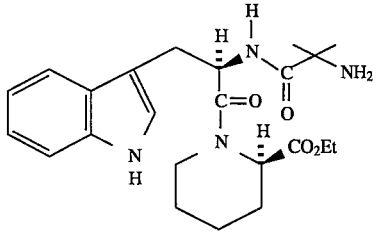
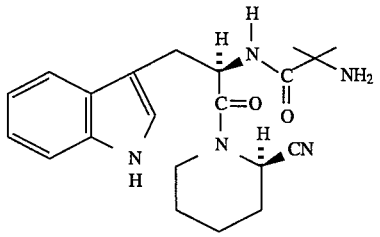
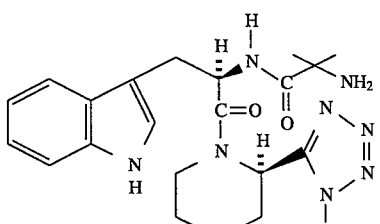
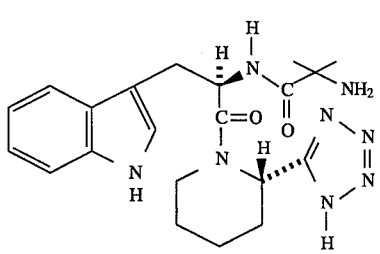
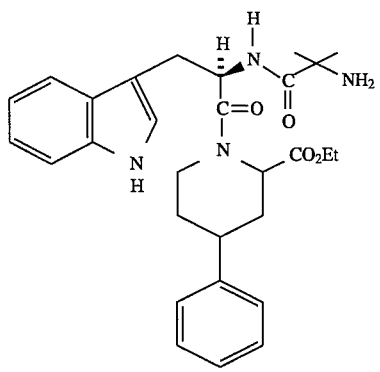
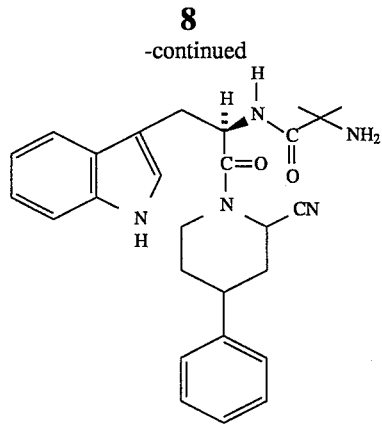
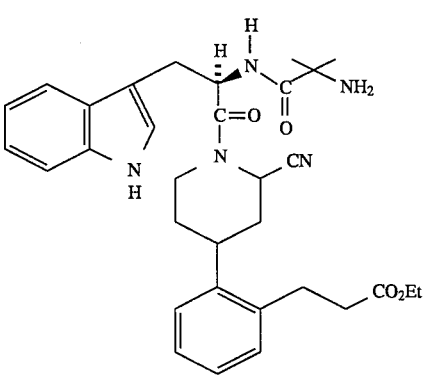
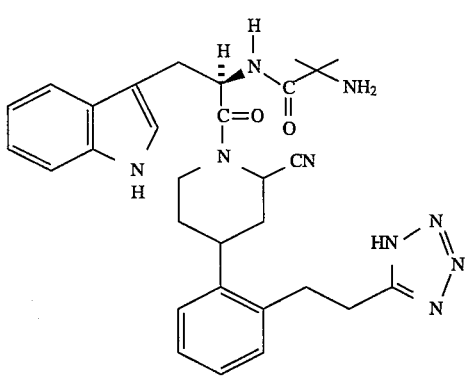
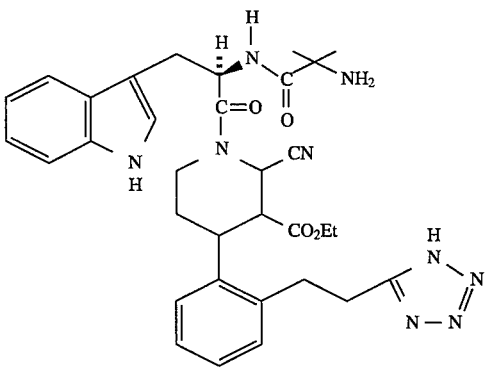

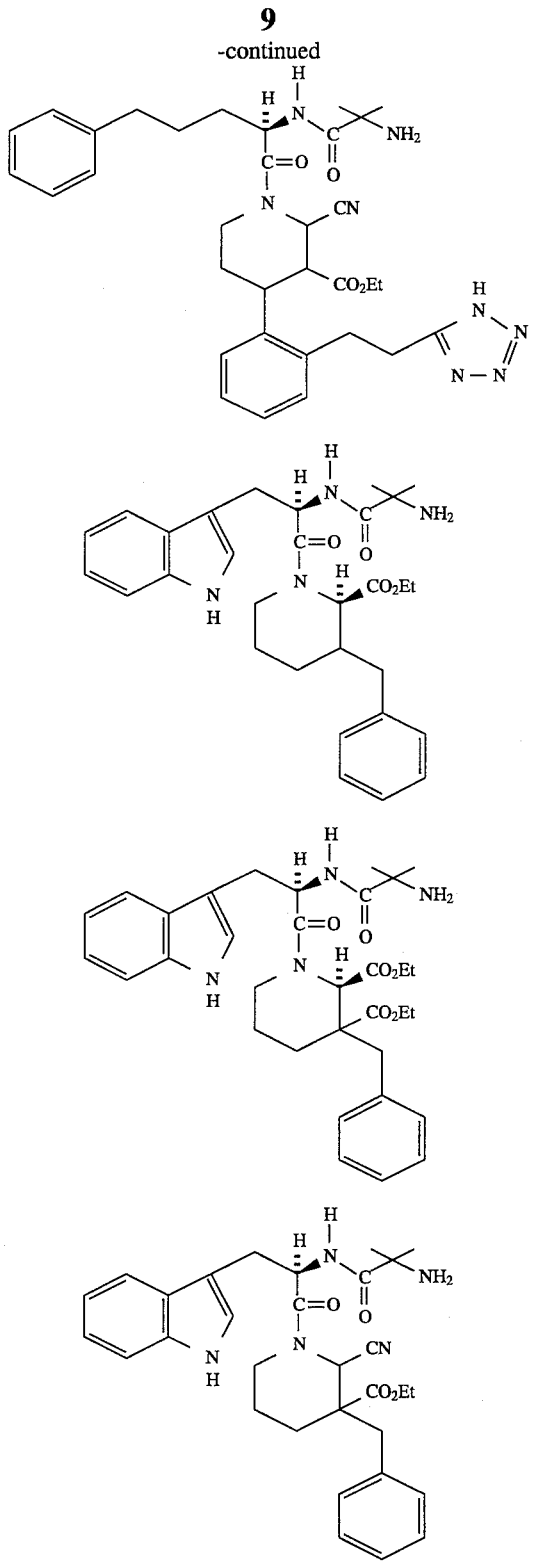

and pharmaceutically acceptable salts and individual diastereomers thereof.

Throughout the instant application, the following abbreviations are used with the following meanings:

| | |
|---|---|
| BOC | t-butyloxycarbonyl |
| BOP | Benzotriazol-1-yloxy tris(dimethylamino)-phosphonium hexafluorophosphate |
| CBZ | Benzyloxycarbonyl |
| DIBAL-H | diisobutylaluminum hydride |
| DMF | N,N-dimethylformamide |
| EDC | 1-(3-dimethylaminopropyl)-3-ethylcarbodiimide hydrochloride |
| FAB-MS | Fast atom bombardment-mass spectroscopy |
| GHRP | Growth hormone releasing peptide |
| HOBT | Hydroxybenztriazole |
| LAH | Lithium aluminum hydride |
| HPLC | High pressure liquid chromatography |
| MHz | Megahertz |
| MPLC | Medium pressure liquid chromatography |
| NMM | N-Methylmorpholine |
| NMR | Nuclear Magnetic Resonance |
| TFA | Trifluoroacetic acid |
| THF | Tetrahydrofuran |
| TLC | Thin layer chromatography |
| TMS | Tetramethylsilane |

The compounds of the instant invention all have at least one asymmetric center as noted by the asterisk in the structural Formula I above. Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the ambit of the instant invention. In the case of the asymmetric center represented by the asterisk in Formula I; it has been found that the absolute stereochemistry of the more active and thus more preferred isomer is as shown in Formula II. The special configuration of the asymmetric center corresponds to that in a D-amino acid. In most cases this is also designated an R-configuration although this will vary according to the value of $R_1$ used in making R- or S-stereochemical assignments.

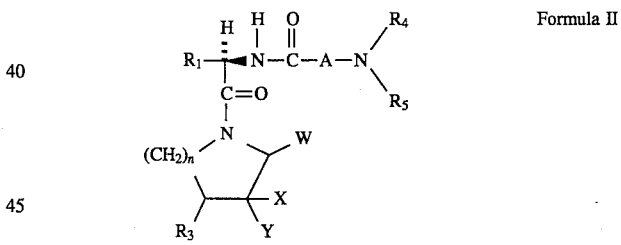

Formula II

The W group may also be present in either R- or S-configurations. Both afford active growth hormone secretagogues although, in general, the R- configuration is more active. In addition, the W group may be cis- or trans- in respect to substituents X, Y or $R_3$. All are within the ambit of this invention and in some of the most preferred compounds these stereochemical orientations are indicated. When the carbon atom in Formula I bearing an asterisk is of a defined and usually a D-configuration, diastereomers result according to the absolute configuration at the carbon atoms bearing the W, X, Y and $R_3$ groups. These diastereomers are arbitrarily referred to a diastereomers $d_1$, $d_2$, $d_3$, $d_4$, etc. and if desired, their independent syntheses or chromatographic separations may be achieved using standard methods or as described herein. Their absolute stereochemistry may be determined by the x-ray crystallography of crystalline products or crystalline intermediates which are derivatized, if necessary, with a reagent containing an asymmetric center of known absolute configuration.

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The preparation of compounds of Formula I of the present invention can be carried out in sequential or convergent synthetic routes. Syntheses detailing the preparation of the compounds of Formula I in a sequential manner are presented in the following reaction schemes.

The phrase standard peptide coupling reaction conditions is used repeatedly here, and it means coupling a carboxylic acid with an amine using an acid activating agent such as EDC, DCC, and BOP in a inert solvent such as dichloromethane in the presence of a catalyst such as HOBT. The uses of protective groups for amine and carboxylic acid to facilitate the desired reaction and minimize the undesired reaction are well documented. Conditions required to remove protecting groups which may be present and can be found in Greene, T; Wuts, P. G. M. *Protective Groups in Organic Synthesis,* John Wiley & Sons, Inc., New York, NY 1991. CBZ and BOC were used extensively in the synthesis, and their removal conditions are known to those skilled in the art. Removal of CBZ groups can be achieved by a number of methods known in the art; for example, catalytic hydrogenation with hydrogen in the presence of a nobel metal or its oxide such as palladium on activated carbon in a protic solvent such as ethanol. In cases where catalytic hydrogenation is contraindicated by the presence of other potentially reactive functionality, removal of CBZ groups can also be achieved by treatment with a solution of hydrogen bromide in acetic acid, or by treatment with a mixture of TFA and dimethylsulfide. Removal of BOC protecting groups is carried out in a solvent such as methylene chloride or methanol or ethyl acetate, with a strong acid, such as trifluoroacetic acid or hydrochloric acid or hydrogen chloride gas.

The protected amino acid derivatives 1 are, in many cases, commercially available, where the protecting group L is, for example, BOC or CBZ groups. Other protected amino acid derivatives 1 can be prepared by literature methods (Williams, R. M. *Synthesis of Optically Active a-Amino Acids,* Pergamon Press: Oxford, 1989). Many of the piperidines, pyrrolidines and hexahydro-1H-azepines of formula 2 are either commercially available or known in the literature and others can be prepared following literature methods desribed for known compounds, some of which are described here. The skills required in carrying out the reaction and purification of the resulting reaction products are known to those skilled in the art. Purification procedures includes crystallization, and normal phase or reverse phase chromatography.

SCHEME 1

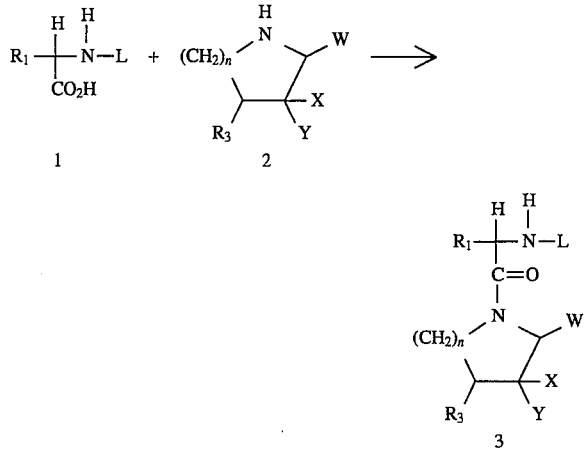

Intermediates of formula 3 may be synthesized as described in Scheme 1. Coupling of amine of formula 2, whose preparations are described later if they are not known compounds, to protected amino acids of formula 1, wherein L is a suitable protecting group, is conveniently carried out under standard peptide coupling conditions.

SCHEME 2

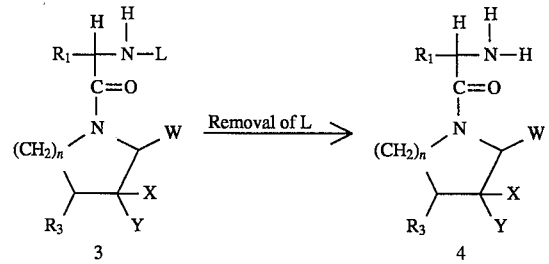

Conversion of 3 to intermediate 4 can be carded out as illustrated in Scheme 2 by removal of the protecting group L (CBZ, BOC, etc.)

SCHEME 3

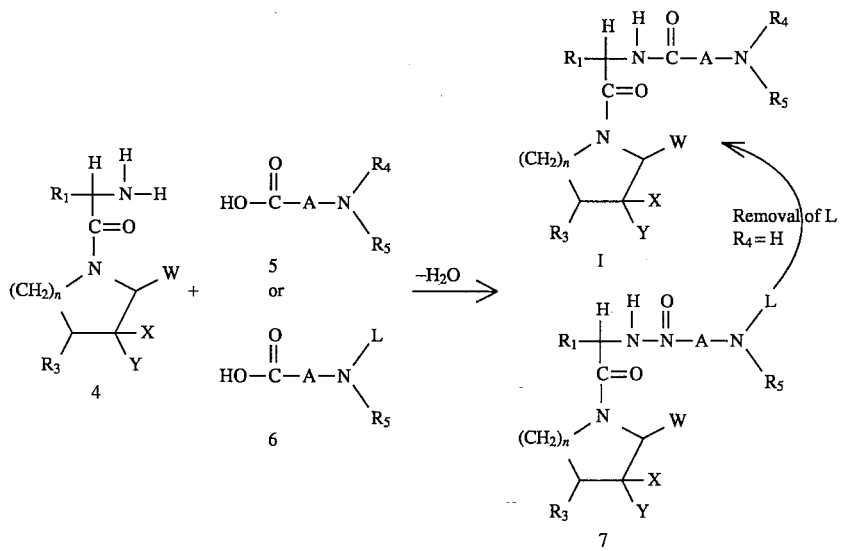

Intermediates of formula 5, wherein A is connected to the carbonyl by a carbon atom and thus A is —$(CH_2)_x$—$C(R_7)(R_{7a})$—$(CH_2)_y$- can be prepared as shown in Scheme 3 by coupling intermediates of formula 4 to amino acids of formula 5 under the standard peptide coupling reaction conditions. The amino acids 5, as amino acid 1, are either commercially available or can be synthesized. Also if $R_4$ or $R_5$ is a hydrogen then the protected amino acids 6 are employed in the coupling reaction, wherein L is a protecting group as defined above. The removal of L in 7 to afford I, where $R_4$=H, can be carded out under conditions known in the art.

SCHEME 4

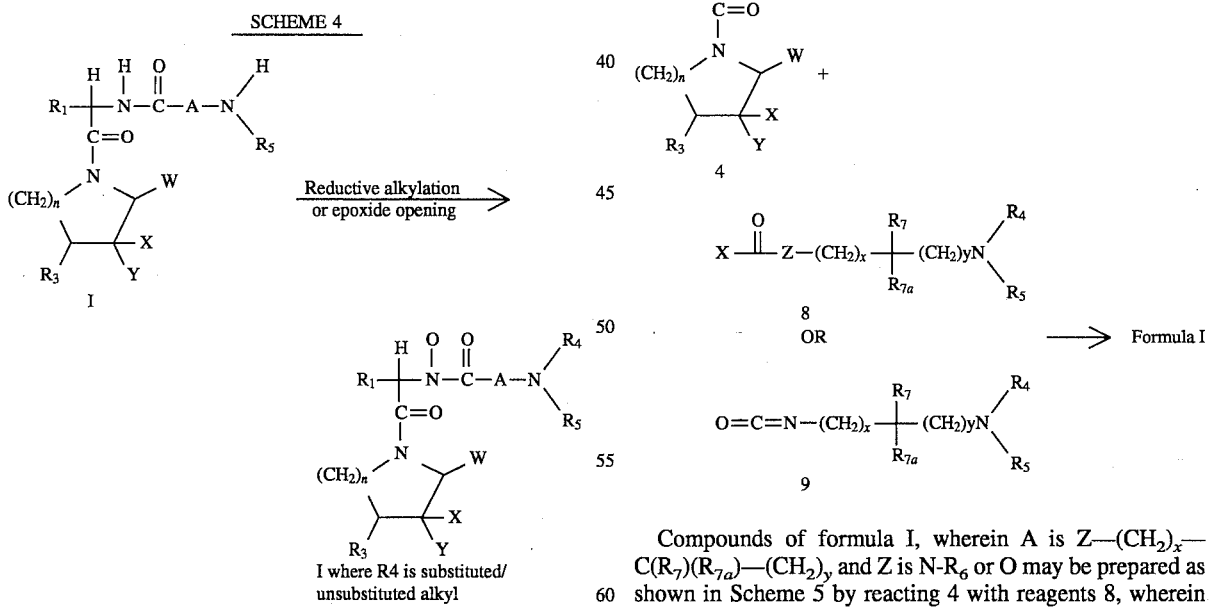

Compounds of formula I wherein $R_4$ and/or $R_5$ is a hydrogen can be further elaborated to new compounds I (with most preferred side chains $R_4$=$CH_2$—$CH(OH)$—$CH_2X$, wherein X = H or OH) which are substituted on the amino group as depicted in Scheme 4. Reductive alkylation of I with an aidehyde is carried out under conditions known in the art; for example, by catalytic hydrogenation with hydrogen in the presence of platinum, palladium, or nickel catalysts or with chemical reducing agents such as sodium cyanoborohydride in a protic solvent such as methanol or ethanol in the present of catalytic amount of acid. Alternatively, a similar transformation can be accomplished via an epoxide opening reaction.

SCHEME 5

Compounds of formula I, wherein A is Z—$(CH_2)_x$—$C(R_7)(R_{7a})$—$(CH_2)_y$ and Z is N-$R_6$ or O may be prepared as shown in Scheme 5 by reacting 4 with reagents 8, wherein X is a good leaving group such as Cl, Br, I, or imidazole. Alternatively, 4 can be reacted with an isocyanate of formula 9 in an inert solvent such as 1,2-dichloroethane to provide compounds of formula I where Z is NH.

The compounds of general formula I of the present invention may also be prepared in a convergent manner as described in Reaction Schemes 6, 7 and 8.

SCHEME 6

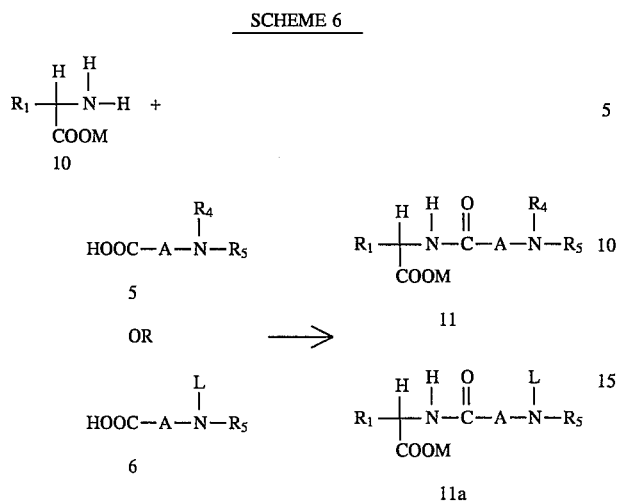

The carboxylic acid protected amino acid derivatives 10 are, in many cases, commercially available where M=methyl, ethyl, or benzyl esters. Other ester protected amino acids can be prepared by classical methods familiar to those skilled in the art. Some of these methods include the reaction of the amino acid with an alcohol in the presence of an acid such as hydrochloric acid or p-toluenesulfonic acid and azeotropic removal of water. Other methods includes the reaction of a protected amino acid with a diazoalkane, or with an alcohol and an acid activating agent such as EDC, DCC in the presence of a catalyst such as DMAP and removal of the protecting group L.

Intermediates of formula 11 or 11a, can be prepared as shown in Scheme 6 by coupling of amino acid ester 10 to amino acids of formula 6 or 7. When a urea linkage is present in 11 or 11a, it can be introduced as illustrated in Scheme 5.

SCHEME 7

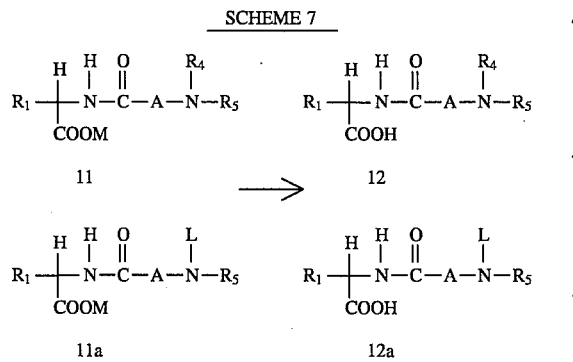

Conversion of the ester 11 or 11a to intermediate acids 12 or 12a can be achieved by a number of methods known in the an as described in Scheme 7: for example, methyl and ethyl esters can be hydrolyzed with lithium hydroxide in a protic solvent like aqueous methanol. In addition, removal of benzyl groups can be accomplished by a number of reductive methods including hydrogenation in the presence of palladium catalyst in a protic solvent such as methanol. An allyl ester can be cleaved with tetra-kis-triphenylphosphine palladium catalyst in the presence of 2-ethylhexanoic acid in a variety of solvents including ethyl acetate and dichloromethane (see *J. Org. Chem.*, 42, 587 (1982)).

SCHEME 8

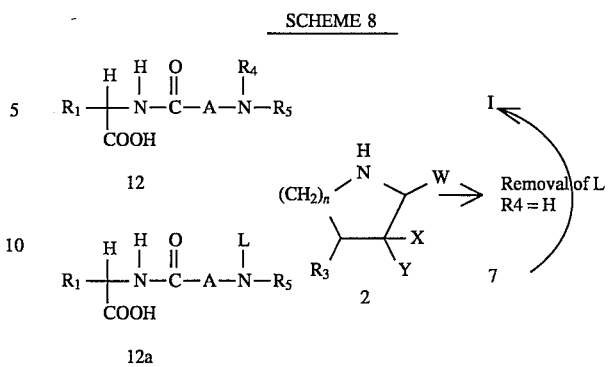

Acid 12 or 12a can then be elaborated to I or compound 7 as described in Scheme 8. Coupling of piperidines, pyrrolidines or hexahydro-1H-azepines of formula 2 to acids of formula 12 or 12a, wherein L is a suitable protecting group, is conveniently carded out under the standard peptide coupling reaction conditions. Transformation of 7 to I is achieved by removal of the protecting group L. When $R_4$ and/or $R_5$ is H, substituted alkyl groups may be optionally added to the nitrogen atom as described in Scheme 4.

The 2-substituted piperidines, pyrrolidines or hexahydro-1H-azapines are either commercially available or can be prepared by literature procedures. Illustrated here are some, but by no means all, the methods for their preparation.

SCHEME 9

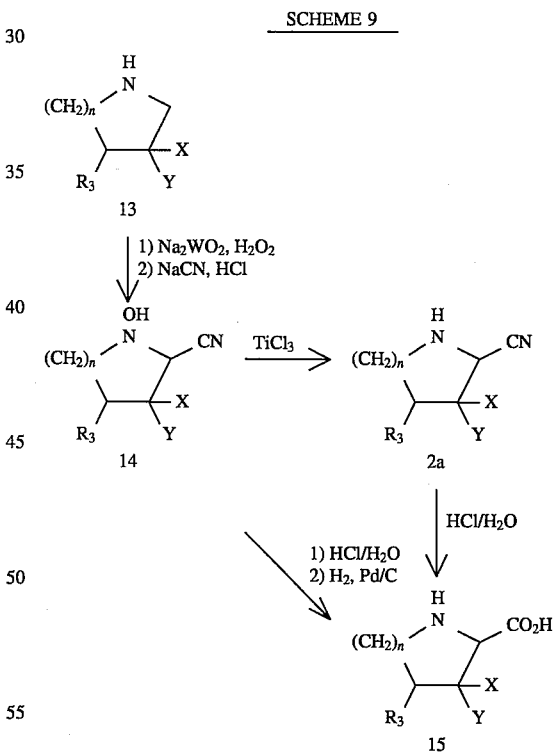

According to the protocol developed by S. Murahashi and T. Shiota (*Tetrahedron Lett.*, 28, 6469–6472 (1987)) catalytic oxidation of cyclic amines such as piperdines, pyrrolidines or hexahydro-1H-azapines with hydrogen peroxide followed by treatment with hydrogen cyanide gives α-hydroxylaminonitriles of formula 14, which upon reduction (Murahashi, S. I.; Kodera, Y., *Tetrahedron Letters.*, 26, 4633–4636 (1985)) give α-aminonitriles of formula 2a. In cases where X and Y are not both hydrogen and/or n is not 2, regioisomers and diastereoisomers may arise, and they may be separated by chromatography methods. Hydrolysis of the amino nitrile under acidic or basic conditions yields the amino acid. Alteratively, the hydroxylaminonitrile can be hydrolyzed first, then reduced by palladium catalyzed hydrogenation to afford the amino acid of formula 15. The amino acid and their derivatives prepared according to this method are racemic.

Alternatively, the nitrile 2a can be prepared by oxidation of the compound 13 to the imine as described in the literature (Goti and Romani in *Tetrahedron Letters*, 35, 6567–6570 (1994)) followed by reaction with cyanide. W can also be introduced by direct alkylation of the Boc protected compound 13 by butyl lithium followed by addition of electrophiles known as the Beak alkylation (Beak and Lee *J. Org. Chem.*, 55, 2578–2580 (1990)). Asymmetric introduction of W can also be achieved by using a chiral catalyst (Kerrick and Beak, *J. Am. Chem. Soc.* 113, 9708–9710 (1991)).

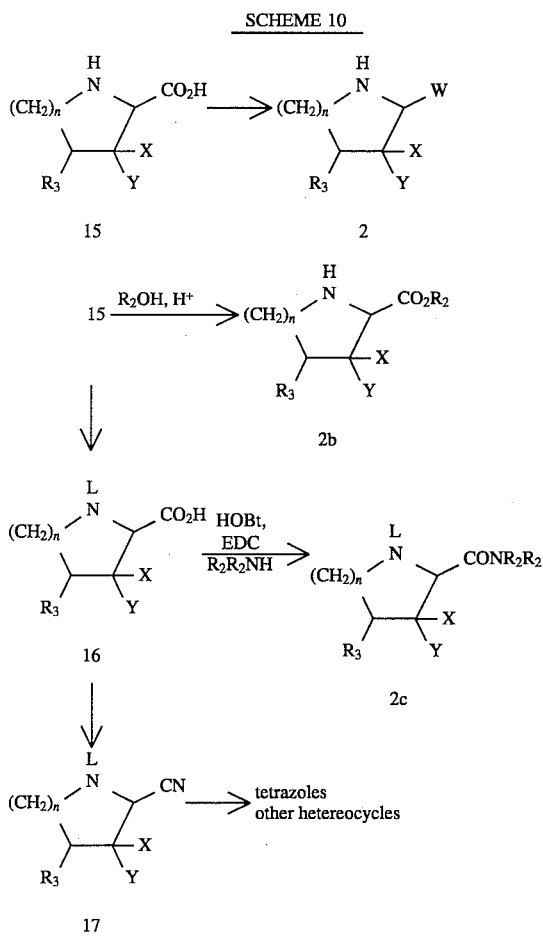

The carboxylic acid functionality at the 2-position of compounds of formula 15 can be convened to ester, amide, nitrile, acyl sulfonamide, and moieties as defined by W to give compound of general formula 2 according to the conventional methods well documented in the literature and known to those skilled in the art (*The Practice of Peptide Synthesis*, by M. Bodanszky and A. Bodanszky, Springer-Verlag, 1984). L is an appropriate protecting group such as BOC, CBZ, etc. The carboxylic acid can also be convened into its next higher homologue, or to a derivative of the homologous acid, such as amide or ester by an Arndt-Eistert reaction. Alternatively, the ester can be directly homologated by the protocol using ynolate anions described by C. J.

Kowalski and R. E. Reddy in *J. Org. Chem.* 1992, 57, 7194–7208. The resulting acid and/or ester can be convened to the next higher homologue, and so on and so forth.

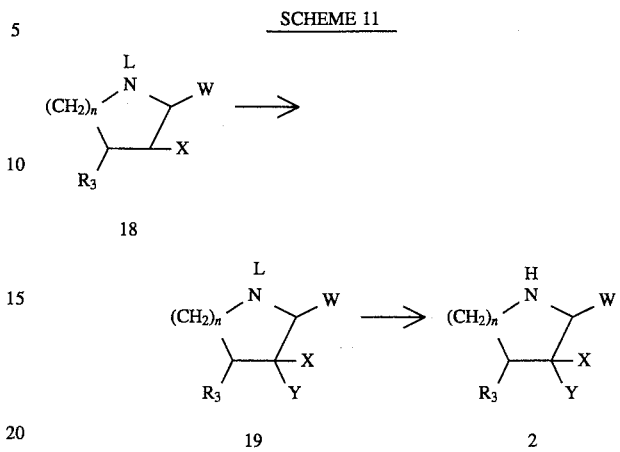

Illustrated in Scheme 11 is a general method to introduce Y wherein X is an electron withdrawing group such as —CN, —CO$_2$R$_8$, where R$_8$ is alkyl, aryl, and alkyl(C$_1$–C$_4$)aryl are either known compounds or may be prepared by methods described above or by methods analogous to those used for the preparation of known compounds. Introduction of the Y substitution can be achieved by first reacting compounds of formula 18 with a strong base such as potassium bis(trimethylsilyl)amide, lithium diisopropylamide following by addition of alkylating reagents such as alkyl halides, aryl alkyl halides, acyl halides, and haloformates in a inert solvent such as THF at temperatures from −100° to room temperature. The derivatives where the sulfur is attached directly to an alkyl or an aryl group can be prepared similarly by reacting with a disulfide. The halides used in these reactions are either commercially available or known compounds in the literature can be prepared by methods analogous to those used for the preparation of known compounds. The protecting group L in compounds of formula 19 can be removed with conventional chemistry to give compounds of formula 2.

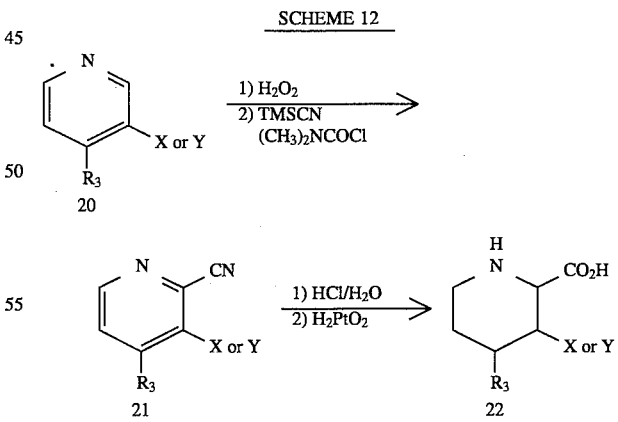

To prepare cis homoproline derivatives, the procedure described by Shuman et al can be used (Shuman, R. T.; Ornstein, P. L.; Paschal, J. W.; Gesellchen, P. D. *J. Org. Chem.* 1990, 55, 738–741) (Scheme 12). Substituted pyridines of formula 20, many of them commercially available or prepared by literature procedures, are convened to their corresponding N-oxide by reacting with hydrogen peroxide. Reaction of the pyridine N-oxide with tfimethylsilylcyanide and dimethylcarbamyl chloride gives the 2-nitrile of formula 21. If regioisomers should arise due to the presence of 3-substitution, they can be conveniently separated by chromatography. Hydrolysis of the nitrile to the acid under acidic or basic conditions followed by hydrogenation catalyzed by platinum oxide gives the piperidine carboxylic acid. The functionalization of the carboxylic acid is described above and in part by Scheme 10.

The amino acids generated by these synthetic protocols are racemic. However, procedures for resolving RS-α-amino acids by various methods are known in the literature (Toone, E. J. and Jones, J. B. *Can. J. Chem.* 1987, 65, 2722; Okamoto, S.; Hijikato, A. *Biochem. Biophys. Res. Cotnmun.* 1981, 101,440; Greenstein, J. P.; Winitz, M. *Chemistry of the Amino Acids*; Wiley: New York, 1961, Vol. 1, 715–760). Therefore, the separated R- and S- isomers can be prepared by this methodology. Alternatively, the racemic piperidine, pyrrolidine and 5hexahydro-1H-azepine derivatives can be convened directly to growth hormone secretagogues or their intermediates, and the resulting diastereomeric mixtures can be separated at the appropriate stage by chromatography to yield the enantiomerically pure compounds.

diene 24 in the presence of TFA (1 equivalent) and water (catalytic) gives the adducts 25 and 26 with good diastereoselectivity. The two diastereoisomers can be separated, and each can be hydrogenated to reduce the double bond and to remove the chiral auxiliary. All four possible isomers can be achieved by this methodology. Illustrated here (Scheme 13) is the preparation of the two isomers 15a and 15b which have an S-configuration at the chiral center adjacent to the COOH. The two R- isomers at this center can be prepared similarly using compound 26.

The compounds of the present invention may also be prepared from a variety of substituted natural and unnatural amino acids of formulas 46. The preparation of many of these acids is described in U.S. Pat. No. 5,206,237. The preparation of these intermediates in racemic form is accomplished by classical methods familiar to those skilled in the an (Williams, R. M. "*Synthesis of Optically Active α-Amino Acids*" Pergamon Press: Oxford. 1989; Vol. 7). Several methods exist to resolve (DL)—

SCHEME 13

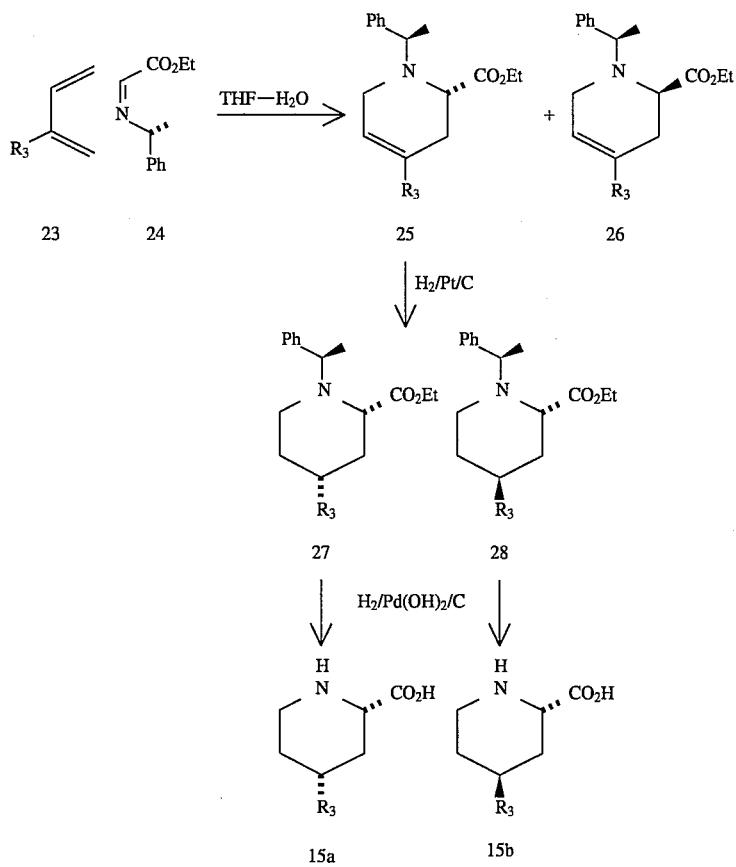

Alternatively, asymmetric synthesis can be carded out to synthesize optically pure piperidine, pyrrolidine and hexahydro-1H-azepine derivatives. For example, optically active piperidine-2-carboxylic acid derivatives 15a, 15b can be prepared by the aza-Diels-Alder reaction as described by Bailey et al (*J. Chem. Soc. Perkin Trans I*, 1991, 1337–1340). Reaction between the chiral imine 23 and the

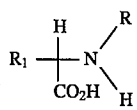

amino acids. One of the common methods is to resolve amino or carboxyl protected intermediates by crystallization of salts derived from optically active acids or amines. Alternatively, the amino group of carboxyl protected intermediates may be coupled to optically active acids by using chemistry described earlier. Separation of the individual diastereomers either by chromatographic techniques or by crystallization followed by hydrolysis of the chiral amide furnishes resolved amino acids. Similarly, amino protected intermediates may be converted to a mixture of chiral diastereomeric esters and amides. Separation of the mixture using methods described above and hydrolysis of the individual diastereomers provides (D) and (L) amino acids. Finally, an enzymatic method to resolve N-acetyl derivatives of (DL)-amino acids has been reported by Whitesides and coworkers in *J. Am. Chem. Soc.* 1989, 111, 6354–6364.

When it is desirable to synthesize these intermediates in optically pure form, established methods include: (1) asymmetric electrophilic amination of chiral enolates (*J. Am. Chem. Soc.* 1986, 108, 6394–6395, 6395–6397, and 6397–6399), (2) asymmetric nucleophilic amination of optically active carbonyl derivatives, (*J. Am. Chem. Soc.* 1992, 114, 1906; *Tetrahedron Lett.* 1987, 28, 32), (3) diastereoselective alkylation of chiral glycine enolate synthons (*J. Am. Chem. Soc.* 1991, 113, 9276; *J. Org. Chem.* 1989, 54, 3916), (4) diastereoselective nucleophilic addition to a chiral electrophilic glycinate synthon (*J. Am. Chem. Soc.* 1986, 108, 1103), (5) asymmetric hydrogenation of prochiral dehydroamino acid derivatives ("*Asymmetric Synthesis, Chiral Catalysis*"; Morrison, J. D., Ed; Academic Press: Orlando, FL, 1985; Vol 5), and (6) enzymatic syntheses (*Angew. Chem. Int. Ed. Engl.* 1978, 17, 176).

SCHEME 14

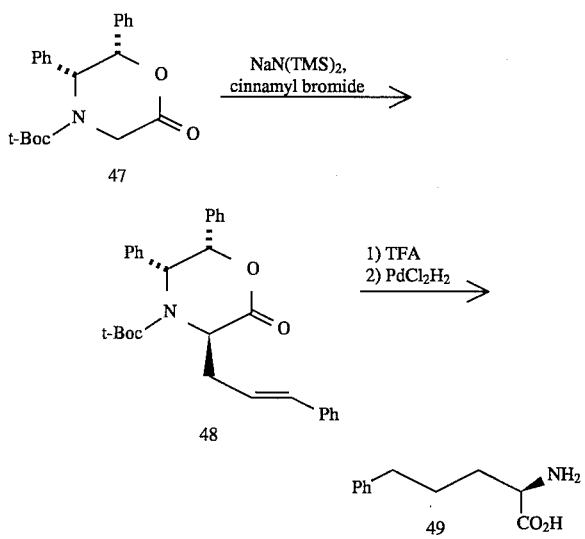

For example, alkylation of the enolate of diphenyloxazinone 47 (*J. Am. Chem. Soc.* 1991, 113, 9276) with cinnamyl bromide in the presence of sodium bis(trimethylsilyl)amide proceeds smoothly to afford 48 which is convened into the desired (D)-2-amino-5-phenylpentanoic acid 49 by removing the N-t-butyloxycarbonyl group with trifluoroacetic acid and hydrogenation over a PdCl$_2$ catalyst (Scheme 14).

SCHEME 15

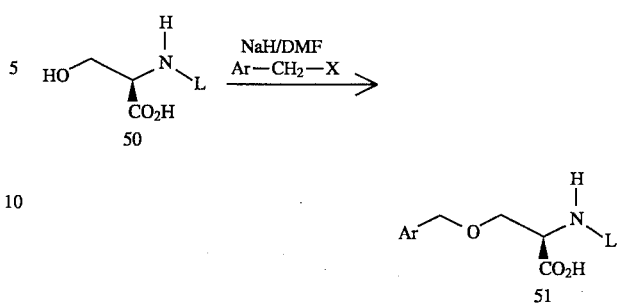

Intermediates of formula 46 which are O-benzyl-(D)-serine derivatives 51 are conveniently prepared from suitably substituted benzyl halides and N-protected-(D)-serine 50. The protecting group L is conveniently a BOC or a CBZ group. Benzylation of 64 can be achieved by a number of methods well known in the literature including deprotonation with two equivalents of sodium hydride in an inert solvent such as DMF followed by treatment with one equivalent of a variety of benzyl halides (Synthesis 1989, 36) as shown in Scheme 15.

The O-alkyl-(D)-serine derivatives may also be prepared using an alkylation protocol. Other methods that could be utilized to prepare (D)-serine derivatives of formula 5 1 include the acid catalyzed benzylation of carboxyl protected intermediates derived from 50 with reagents of formula ArCH$_2$OC(=NH)CCl$_3$ (O. Yonemitsu et al., *Chem. Phann. Bull.* 1988, 36, 4244). Alternatively, alkylation of the chiral gylcine enolates (*J. Am. Chem. Soc.* 1991. 113, 9276; *J. Org. Chem.* 1989, 54, 3916) with ArCH$_2$OCH$_2$X where X is a leaving group affords 51. In addition D,L-O-aryl(alkyl)serines may be prepared and resolved by methods described above.

It is noted that in some situations the order of carrying out the foregoing reaction schemes may be varied to facilitate the reaction or to avoid unwanted reaction products.

The utility of the compounds of the present invention as growth hormone secretagogues may be demonstrated by methodology known in the art, such as an assay described by Smith, et al., *Science*, 260, 1640–1643 (1993) (see text of FIG. 2 therein). In particular, all of the compounds prepared in the following examples had activity as growth hormone secretagogues in the aforementioned assay. Such a result is indicative of the intrinsic activity of the present compounds as growth hormone secretagogues.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, to improve feed efficiency and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise an anabolic agent in addition to at least one of the compounds of Formula I or another composition which exhibits a different activity, e.g., an antibiotic growth permittant or an agent to treat osteoporosis or in combination with a conicosteroid to minimize the catabolic side effects or with other pharmaceutically active materials wherein the combination enhances efficacy and minimizes side effects.

Growth promoting and anabolic agents include, but are not limited to TRH, diethylstilbesterol, estrogens, β-agonists, theophylline, anabolic steroids, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the growth hormone secretagogues of this invention is in combination with other growth hormone secretagogues such as the growth hormone releasing peptides GHRP-6, GHRP- 1 as described in U.S. Pat. Nos. 4,411,890 and publications WO 89/07110, WO 89/07 111 and B-HT920 as well as hexarelin and the newly discovered GHRP-2 as described in WO 93/04081 or growth hormone releasing hormone (GHRH, also designated GRF) and its analogs or growth hormone and its analogs or somatomedins including IGF-1 and IGF-2 or a- adrenergic aginists such as clonidine or serotonin 5HTID agonists such as sumitriptan or agents which inhibit somatostatin or its release such as physostigmine and pyridostigmine.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; treating growth hormone deficient adults; prevention of catabolic side effects of glucocorticoids; treatment of osteoporosis; stimulation of the immune system, acceleration of wound healing; accelerating bone fracture repair; treatment of growth retardation; treating acute or chronic renal failure or insufficiency; treatment of physiological short stature, including growth hormone deficient children; treating short stature associated with chronic illness; treatment of obesity and growth retardation associated with obesity; treating growth retardation associated with Prader-Willi syndrome and Turner's syndrome; accelerating the recovery and reducing hospitalization of burn patients or following major surgery such as gastrointestinal surgery; treatment of intrauterine growth retardation, and skeletal dysplasia, treatment of peripheral neuropathies; replacement of growth hormone in stressed patients; treatment of osteochondrodysplasias, Noonans syndrome, schizophrenia, depression, Alzheimer's disease, delayed wound healing, and psychosocial deprivation; treatment of pulmonary dysfunction and ventilator dependency; attenuation of protein catabolic response after a major operation; treating malabsorption syndromes; reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; to stimulate thymic development and prevent the age-related decline of thymic function; adjunctive therapy for patients on chronic hemodialysis; treatment of immunosuppressed patients and to enhance antibody response following vaccination; increasing the total lymphocyte count of a human, in particular, increasing the $T_4/T_8$-cell ratio in a human with a depressed $T_4/T_8$-cell ratio resulting, for example, from physical trauma, such as closed head injury, or from infection, such as bacterial or viral infection, especially infection with the human immunodeficiency virus; improvement in muscle strength, mobility, maintenance of skin thickness, metabolic homeostasis, renal hemeostasis in the frail elderly; stimulation of osteoblasts, bone remodelling, and cartilage growth; stimulation of the immune system in companion animals and treatment of disorders of aging in companion animals; growth promotant in livestock; and stimulation of wool growth in sheep. Further, the instant compounds are useful for increasing feed efficiency, promoting growth, increasing milk production and improving the carcass quality of livestock.

In particular, the instant compounds are useful in the prevention or treatment of a condition selected from the group consisting of: osteoporosis; catabolic illness; immune deficiency, including that in individuals with a depressed $T_4/T_8$ cell ratio; hip fracture; musculoskeletal impairment in the elderly; growth hormone deficiency in adults or in children; obesity; cachexia and protein loss due to chronic illness such as AIDS or cancer; and treating patients recovering from major surgery, wounds or burns, in a patient in need thereof.

It will be known to those skilled in the art that there are numerous compounds now being used in an effort to treat the diseases or therapeutic indications enumerated above. Combinations of these therapeutic agents some of which have also been mentioned above with the growth hormone secretagogues of this invention will bring additional, complementary, and often synergistic properties to enhance the growth promotant, anabolic and desirable properties of these various therapeutic agents. In these combinations, the therapeutic agents and the growth hormone secretagogues of this invention may be independently present in dose ranges from one one-hundredth to one times the dose levels which are effective when these compounds and secretagogues are used singly.

Combined therapy to inhibit bone resorption, prevent osteoporosis and enhance the healing of bone fractures can be illustrated by combinations of bisphosphonates and the growth hormone secretagogues of this invention. The use of bisphosphonates for these utilities has been reviewed, for example, by Hamdy, N.A.T., Role of Bisphosphonates in Metabolic Bone Diseases. *Trends in Endocrinol. Metab.*, 1993, 4, 19–25. Bisphosphonates with these utilities include alendronate, tiludronate, dimethyl - APD, risedronate, etidronate, YM-175, clodronate, pamidronate, and BM-210995. According to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage for Iris for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg. of body weight daily are administered to patients and animals, e.g., mammals, to obtain effective release of growth hormone.

The following examples are provided for the purpose of further illustration only and are not intended to be limitations on the disclosed invention.

INTERMEDIATE 1

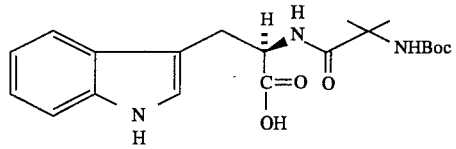

Step A:

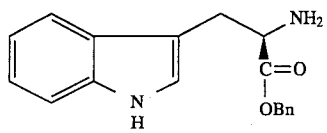

To a solution of the commercially available N-t-BOC-D-tryptophan (25.0 g, 82.2 mmol), benzyl alcohol (10.2 mL, 98.6 mmol), and DMAP (100 mg) in dichloromethane (200 mL) at 0° C., was added EDC (17.4 g, 90.4 mmol) in several portions over a one hour period. The reaction mixture was stirred at room temperature for six hours and was poured into water (200 mL), and the organic layer was separated. The organic solution was washed with a mixture of brine and 3 N hydrochloric acid, dried over anhydrous magnesium sulfate, filtered and concentrated to give a thick oil, which solidified upon standing.

To a solution of this oil in 30 mL of dichloromethane was added 20 mL of TFA and stirred for 1h. The reaction mixture was concentrated, neutralized carefully with saturated aqueous sodium bicarbonate solution, and extracted with dichloromethane (2×100 mL). The combined organic solution was washed with brine (100 mL), passed through a short column of silica gel eluting with 5–10% methanol in dichloromethane to give 23.2 g of the amine as an oil after evaporation.

Step B:

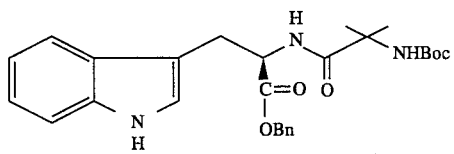

To a solution of the above product, HOBT (10.6 g, 78.8 mmol) and N-BOC-α-methyl alanine (19g, 94.5 mmol) in 200 mL of dichloromethane, was added EDC (19.5 g, 0.102 mol) in several portions at 0° C. After 5 minutes, the clear reaction mixture became milky. After stirring at room temperature overnight, the reaction mixture was poured into 200 mL of water and the organic layer was separated. The organic solution was washed with brine, and with a brine and saturated sodium bicarbonate solution, dried over anhydrous magnesium sulfate, filtered and concentrated to give a thick oil, which was purified by flash chromatography eluting with a gradient of 10–40% ethyl acetate in hexane to give the desired material (28.7 g).

¹H NMR (CDCl₃, 200 MHz) δ8.48 (br.s, 1H), 7.54 (br.d, 1H), 7.38–7.23 (m, 3H), 7.19 (br.d, 2H), 7.15–7.00 (m, 1H), 6.90 (d, 1H), 6.86 (d, 1H), 5.06 (br.s, 2H), 4.95 (ddd, 1H), 3.30 (2dd, 2H), 1.40 (s, 15H)

Step C:

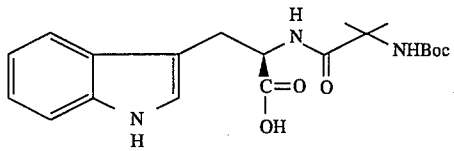

A solution of the material from Step B (28.7g) in 200 mL of ethanol was stirred at RT under a H₂ balloon for 20 minutes in the presence of 10% palladium on carbon (2 g). The catalyst was filtered off through a pad of celite and washed with ethyl acetate. The filtrate was concentrated to give the acid as a slightly pink foam (23.3 g).

¹H NMR (CD₃OD, 400 MHz) δ7.56 (d, J=8 Hz, 1 H), 7.31 (dd, J=1, 8 Hz, 1 H), 7.09 (s, 1 H), 7.07 (dr, J=1, 7 Hz, 1 H), 6.98 (dt, J=1, 7 Hz, 1 H), 4.69 (t, J=6 Hz, 1 H), 3.34–3.23 (m, 2 H), 1.35 (s, 3 H), 1.34 (s, 9 H), 1.29 (s, 3 H).

FAB-MS calc. for C₂₀H₂₇N₃O₅: 389; Found 390 (M+H), 290 (M+H-100 (BOC)).

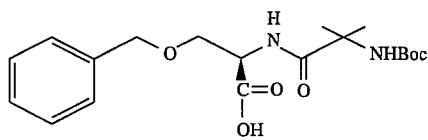

Following the procedures for the preparation of Intermediate 1 using N-t-Boc-O-Benzyl-D-sefine in the place of N-t-BOC-D-tryptophan gave Intermediate 2.

FAB-MS calc. for C₁₉H₂₈N₂O₆: 380; Found 381 (M+H), 325 (M+H-56 (t-Bu)), 281 (M+H-100 (BOC)).

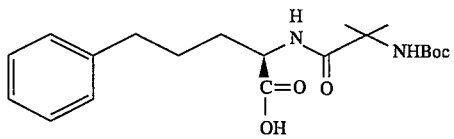

Step A: (DL)-N-acetyl-2-amino-5-phenylpentanoic acid

To a solution of sodium (2.3 g, 0.1 mol) in ethanol (60 mL) under nitrogen at room temperature, was added diethyl acetamidomalonate. The mixture was stirred at room temperature for one hour, and then 1-bromo-3-phenylpropane was added dropwisely. After the addition, the mixture was stirred at room temperature for two hours, then refluxed overnight. It was cooled to room temperature and partitioned between water and ethyl acetate. The organic layer was washed with sodium bicarbonate in water, dried over MgSO4 and evaporated to give an intermediate (32.5 g, 97%).

¹H NMR (CDCl₃, 400MHz) 7.26–7.10 (m, 5 H); 6.75 (br. s, 1 H); 4.19 (q, J=7 Hz, 4 H); 2.58 (t, J=7.9 Hz, 2 H); 2.39–2.35 (m, 2 H); 2.00 (s, 3 H); 1.43–1.39 (m, 2 H); 1.20 (t, J=7 Hz, 6 H).

The product above was suspended in 190 mL of 2.5 N NaOH in water and refluxed for two hours. The mixture was cooled to 0° C., and it was carefully neutralized with 6 N HCl to pH2. The precipitate was collected using a sintered glass funnel and washed with a small amount of cold water and air dried. The solid was then suspended in 300 mL of water and refluxed for four hours. The solution was cooled and acidified to pH1 and the solid was collected by filtration (15.3 g, 67%).

¹H NMR (CD₃OD, 400MHz) 7.26–7.12 (m, 5 H); 4.90–4.37 (m, 1 H); 2.65–2.60 (m, 2 H); 1.97 (s, 3 H); 1.87–1.82 (m, 1 H); 1.73–1.65 (m, 3 H).

Step B: (D)-N-acetyl-2-amino-5-phenylpentanoic acid

The racemic intermediate from the previous step (10 g, 42.5 mmol) and COCl3–6H₂O were dissolved in 21 ml of 2 N KOH and 200 mL of water at 40° C., and the pH of the solution was adjusted to 8 by the addition of the several drops of 2 N KOH. Then acylase I (Aspergillus sp, 0.5 u/mg, from Sigma; 0.9 g) was added with vigorous stirring. The reaction mixture was stirred for one day at 40° C. and the pH was kept at 8 by the addition of a few drops of KOH. The solid which formed was filtered off. The filtrate was acidified by 3 N HCl to pH2, and was extracted with ethyl acetate (200 mL×4). The organic extracts were combined and evaporated to give a white solid (4.64 g, 46%)

¹H NMR (CD3OD, 400MHz) 7.26–7.12 (m, 5 H); 4.90–4.37 (m, 1 H); 2.65–2.60 (m, 2 H); 1.97 (s, 3 H); 1.87–1.82 (m, 1 H); 1.73–1.65 (m, 3 H).

Step C: (D)-N-t-Boc-2-amino-5-phenylpentanoic acid

The intermediate from step B (4.2 g, 17.8 mmol) was suspended in 2 N HCl (100 mL) and refluxed for two hours. The reaction mixture was evaporated in vacuo to remove water and hydrochloric acid to yield a white solid. To a solution of this solid in 50 mL of water, was added 3 N NaOH until the pH 11, then di-t-butyl dicarbonate (4.66 g, 21.4 mmol) was added with vigorous stirring. After four hours, the reaction mixture was acidified to pH2 with 3 N HCl and it was extracted with ethyl acetate (100 mL×3). The organic extracts were combined and evaporated to give a white solid (6.56 g, crude) which was used without purification.

¹H NMR (CD3OD, 400MHz) 7.26–7.12 (m, 5 H); 4.11–4.08 (m, 1 H); 2.65–2.60 (m, 2 H); 1.83–1.62 (m, 4 H); 1.43 (s, 9 H).

Step D:

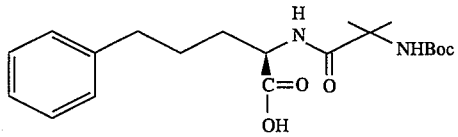

Following the procedures for the preparation of intermediate 1 using (D)-N-t-Boc-2-amino-5-phenylpentanoic acid in the place of N-t-BOC-D-tryptophan gave intermediate 3.

¹H NMR (CDCl₃, 400MHz) 7.24–7.20 (m, 2H), 7.15–7.04 (m, 3H), 4.60– 4.55 (m, 1H), 2.62–2.55 (m, 2H), 2.00–1.86 (m, 1H), 1.78–1.60 (m, 1.50 (s, 6H), 1.30 (s, 9H).

EXAMPLE 1

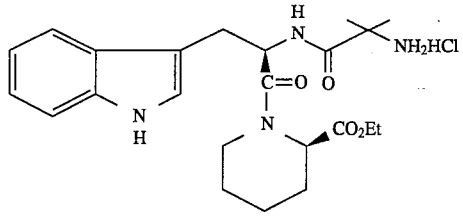

Step A:

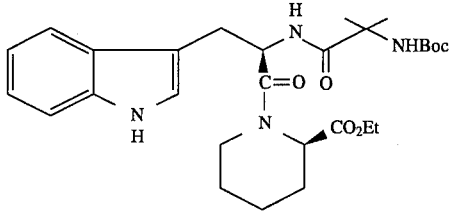

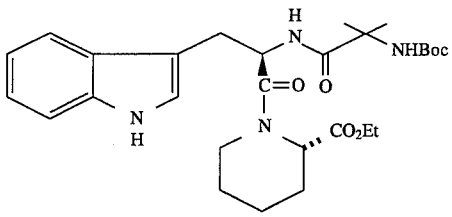

To a solution of ethyl (d1) pipecolinate (1 g), HOBT (860 mg) and Intermediate 1 (2.47 g) in dichloromethane (80 mL) at 0° C. was added EDC (2.3 g). The reaction mixture was stirred at room temperature overnight. The solution was washed with water, saturated sodium bicarbonate solution, and saturated sodium chloride solution, dried over anhydrous magnesium sulfate; then filtered and concentrated to give a crude product. The crude product was purified by MPLC eluting with 60% ethyl acetate in hexane to give the product as a mixture of two diastereomers (2.79 g). Separation of 500 mg of the mixture by MPLC eluting with 50% ethyl acetate in hexane yielded the two individual diastereomers. The diastereomer which came out of the column first was designated as d₁ (187 mg) and the stereochemistry of the pipecolinic acid ester was subsequently shown to be R. The one which came out last was designated as d₂ (116 mg) and the stereochemistry of the pipecolinic acid ester in it is S. In addition, there were mixed fractions which were combined and evaporated to yield 190 mg of a mixture of d₁ and d₂.

d₁: FAB-MS calc. for $C_{28}H_{40}N_4O_6$: 528; Found: 529 (M+H)

d₂: FAB-MS calc. for $C_{28}H_{40}N_4O_6$: 528; Found: 529 (M+H)

Step B:

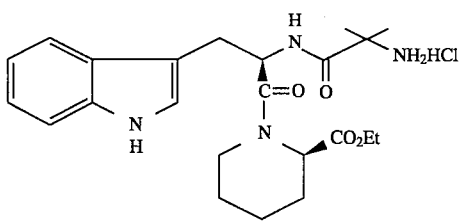

A solution of the compound d₁ from Step A (140 mg) in ethyl acetate (5 mL) was cooled to 0° C. While stirring, hydrogen chloride gas was bubbled into the mixture until saturation occurred. The reaction was stirred for 15 minutes. The solution was then concentrated to remove ethyl acetate. The residue was then redissolved in dichloromethane and hexane followed by evaporation in vacuo to afford the product as a solid (110mg).

FAB-MS calc. for $C_{23}H_{32}N_4O_4$: 428; Found: 429 (M+H)

¹HNMR (400 MHz, CD₃OD): compound exists as a mixture of rotamers (jabout 2:1). 7.57 (d, 1 H), 7.36 & 7.32 (2d, 1H), 7.14–7.00 (m, 3 H), 5.30–5.20 (m), 5.17–5.13 (m), 4.36 (d), 4.21 (q, J=7 Hz), 4.13 (q, J=7 Hz), 4.00 (md), 3.35–3.04 (m), 2.60 (dt), 3.30 ( br. d), 2.70–2.50 (m), 1.57 (s), 1.55 (s), 1.52 (s), 1.50–1.20 (m), 1.33 (s), 1.27 (t, J=7 Hz), 1.21 (t, J=7 Hz), 1.15–1.10 (m), 0.75–0.65 (m), 0.30–0.20 (m).

EXAMPLE 2

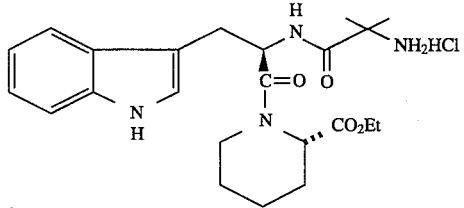

Prepared by the procedure described in Example 1, Step B from the intermediate d2 from Example 1, step A (40 mg) and HCl gas at 0° C. in ethyl acetate (3 mL). Product: 28 mg.

FAB-MS calc. for $C_{23}H_{32}N_4O_4$: 428; Found: 429 (M+H)

¹HNMR (400 MHz, CD₃OD): compound exists as a mixture of rotamers (about 5:1). 7.56 (d, J= 8 Hz ⅚ H), 7.50 (d, ⅙ H), 7.34 (d, J=8 Hz, ⅚ H), 7.31 (d, ⅙ H), 7.12–7.00 (m, 3 H), 5.28 (dd, ⅚ H), 5.15–5.11 (m, ⅙ H), 5.11–5.07 (m, ⅙ H), 5.02–4.98 (m, ⅚ H), 4.52– 4.45 (m), 4.12 (q, J=7 Hz), 4.25–4.00 (m), 3.65 (m), 3.30–3.05(m), 2.80–2.70 (m), 2.32–2.25 (m), 2.02–1.97 (m), 1.75–1.65 (m), 1.57 (s), 1.52 (s), 1.51 (s), 1.40– 0.85 (m), 1.22 (t, J=7 Hz), 0.41–0.30 (m).

EXAMPLE 3

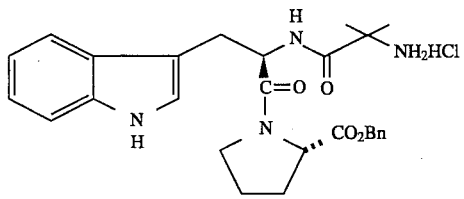

Step A:

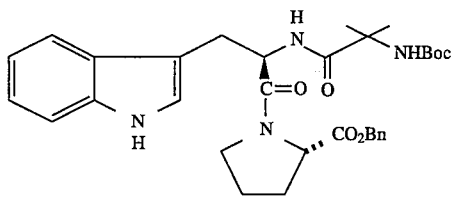

To a stirred solution of L-proline benzyl ester hydrochloride (155 mg, 0.64 mmole), Intermediate 1 (250 mg, 0.64 mmole), HOBT (1 eq.), and NMM (0.07 mL, 0.64 mmole) in dichloromethane at 0°, was added EDC (246 mg, 1.28 mmole). The reaction mixture was stirred at 0° overnight, and then partitioned between 3 N HCl and ethyl acetate. The organic layer was washed with brine and saturated sodium bicarbonate and dried and evaporated. MPLC purification eluting with 50% ethyl acetate gave the intermediate tripeptide benzyl ester (338 mg, 91.5%).

FAB-MS calc. for $C_{32}H_{40}N_4O_6$: 576; Found: 577 (M+H)

Step B:

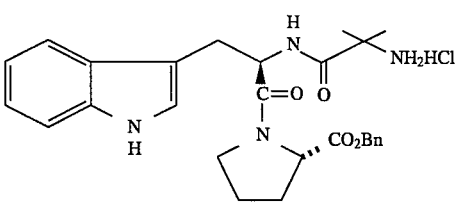

Prepared by the procedure described in Example 1, Step B from the intermediate from the previous step (280 mg) and HCl gas in ethyl acetate (10 mL) at 0° C. Reaction time: 25 minutes. Product: 218 mg.

FAB-MS calc. for $C_{27}H_{32}N_4O_4$: 476; Found: 477 (M+H)

$^1$HNMR (400 MHz, CD$_3$OD ): 8.20 (d), 7.54 (d, J=7.9 Hz, 1H) 7.34–7.00 (m, 9H), 5.11 (dd, J=4.2 Hz, 16.5 Hz, 2H), 4.99–4.94 (m, 1H), 4.23–4.20 (m, 1 H), 3.58–3.53 (m, 1H), 3.31–3.13 (m, 2H), 2.77–2.75 (m, 1H), 1.71– 1.60 (m, 3H) 1.55 (s, 3H), 1.51 (s, 3H), 1.37–1.33 (m, 1H).

EXAMPLE 4

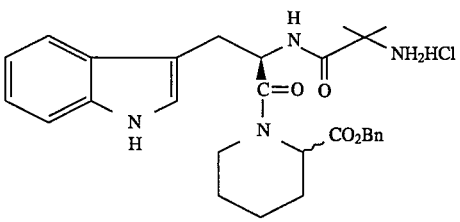

Step A: (dl)-Pipecolinic acid, benzyl ester

A solution of (dl)-pipecolinic acid (25g), p-toluenesulfonic acid (38g), and benzyl alcohol (84g) in toluene (200 mL) was refluxed under azeotropic conditions for one day. The solution was cooled to room temperature and the resulting crystals were collected to give the desired product (52.4 g). The product was washed with 3 N NaOH to remove toluenesulfonic acid, and then reacted with HCl gas in ethyl acetate to convert it to the hydrochloride salt.

Step B:

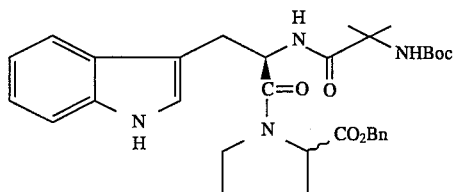

Prepared by the procedure described in Example 3, Step A from (dl)-pipecolinic acid benzyl ester hydrochloride (3.5 g). Intermediate 1 (5.00 g), HOBt (1.74 g), NMM (1.42 mL) and EDC (3.94 g). Product: 6.32 g FAB-MS calc. for $C_{33}H_{42}N_4O_6$: 590; Found: 591 (M+H)

Step C:

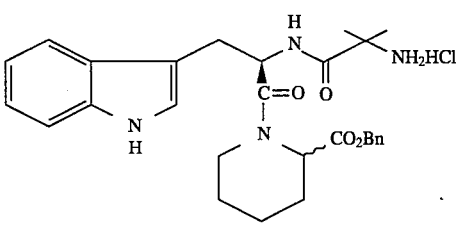

Prepared by the procedure described in Example 1, Step B from the intermediate from the previous step (250 mg) and HCl gas in ethyl acetate at 0° C. to give the title compound (211 mg)

FAB-MS calc. for $C_{28}H_{34}N_4O_4$: 490; Found: 491 (M+H)

EXAMPLE 5

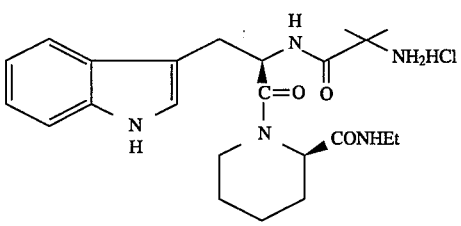

Step A:

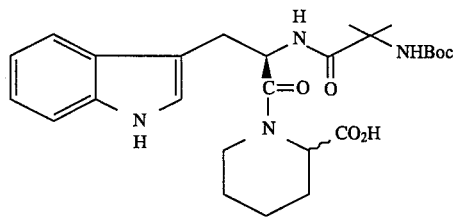

A suspension of the product from Example 4, step B (5.30 g) and 10% palladium on carbon (270 mg) in ethanol (100 mL) was stirred under a hydrogen balloon for 3 hours. The reaction mixture was filtered through celite, evaporated to give the acid (4.48g).

Step B:

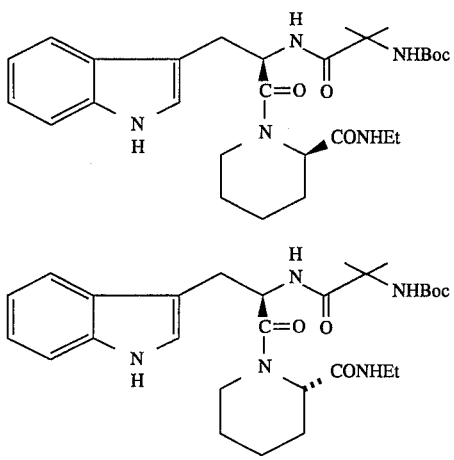

Prepared similarly by the procedure described in Example 3, Step A from the acid intermediate from the previous step (200 mg), ethyl amine hydrochloride (27 mg), HOBt (54 mg), NMM (0.07 mL), and EDC (154 mg) to give a mixture of two diastereomers, which were separated by MPLC eluting with ethyl acetate. The isomer which came out of the column first was designated as $d_1$ (76 mg), and the isomer which came out second as $d_2$ (165 mg).

$d_1$ FAB-MS calc. for $C_{28}H_{41}N_5O_5$: 527; Found: 528 (M+H)

$d_2$ FAB-MS calc. for $C_{28}H_{41}N_5O_5$: 527; Found: 528 (M+H)

Step C:

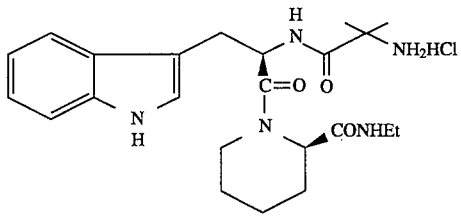

Prepared similarly by the procedure described in Example 1, Step B from intermediate from the previous step ($d_1$) (60 mg) and HCl gas in ethyl acetate (5 mL) at 0° C. to give the title compound (38 mg). Reaction time: 20 minutes.

FAB-MS calc. for $C_{23}H_{33}N_5O_3$: 427; Found: 428 (M+H)

$^1$HNMR (400 MHz, $CD_3OD$ ): d 7.63–7.00 (m, 5 H), 5.33 (t), 5.40–5.25 (m), 5.11–5.09 (m), 4.32 (br. d), 4.16–4.12 (m), 4.00 (md), 3.35– 3.03 (m), 2.96 (q, J=7 Hz), 2.30 (dr), 2.19 (br. d), 1.95–1.40 (m), 1.66 (s), 1.64 (s), 1.40–1.20 (m), 1.20–1.00 (m), 1.12 (t, J=7 Hz), 1.03 (t, J= 7 Hz), 0.65–0.52 (m), −0.44—0.53 (m).

EXAMPLE 6

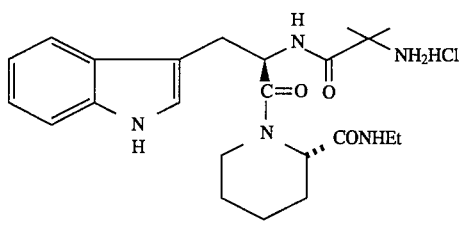

Prepared similarly by the procedure described in Example 1, Step B from intermediate in Example 5 step B ($d_2$) (100 mg) and HCl gas in ethyl acetate (5 mL) at 0° C. to give the title compound (78 mg). Reaction time: 20 minutes.

FAB-MS calc. for $C_{23}H_{33}N_5O_3$: 427; Found: 428 (M+H)

$^1$HNMR (400 MHz, $CD_3OD$ ): d 7.54 (d, J=8 Hz, 1 H), 7.35 (d, J=8 Hz, 1 H), 7.16 (s, 1 H), 7.13–7.00 (m, 2 H), 4.98 (dd, J=6 Hz, 10 Hz), 4.93 (d, 4 Hz), 3.53 (br. d, J=12 Hz, 1 H), 3.35–3.22 (m), 3.14–3.09 (m, 1 H), 2.85 (dt, J=3, 13 Hz, 1 H), 2.02 (br. d, J=12 Hz), 1.65 (s, 3 H), 1.61 (s, 3 H), 1.10 (t, 7 Hz, 3 H), 1.05–0.92 (m, 2 H), 0.72–0.62 (m, 1 H), −0.25—0.30 (m, 1 H).

EXAMPLE 7

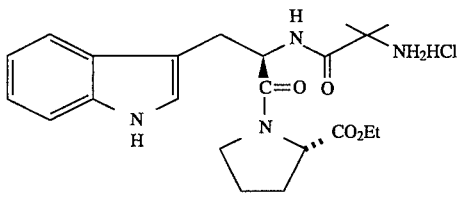

Step A:

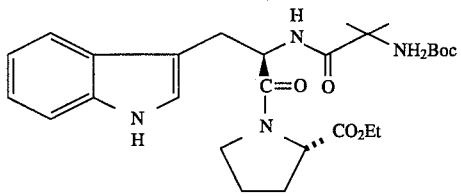

Prepared by the procedure described in Example 3, Step A from L-proline ethyl ester hydrochloride (115 mg, 0.642 mmole), Intermediate 1 (250 mg, 0.642 mmole), HOBT (1 eq.), NMM(0.07 mL, 0.642 mmole), and EDC (246 mg, 1.28 mmole). Product: 330 mg FAB-MS calc. for $C_{27}H_{40}N_4O_6$: 514; Found: 515 (M+H)

Step B:

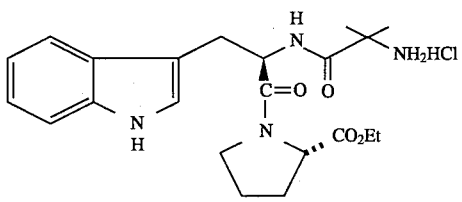

Prepared by the procedure described in Example 1, Step B from the intermediate from the previous step (280 mg) and HCl gas in ethyl acetate (10 mL) at 0° C. Reaction time: 25 minutes. Product: 220 mg.

FAB-MS calc. for $C_{22}H_{32}N_4O_4$: 414; Found: 415 (M+H)

$^1$HNMR (400 MHz, $CD_3OD$ ): 7.53 (d, J=7.9 Hz, 1H), 7.34 (d, J=8.1 Hz, 1H), 7.14–7.01 (m, 3H), 4.97–4.84 (m, 1H), 4.15–4.06 (m, 3H), 3.60– 3.53(m, 1H), 3.31–3.13 (m, 2H), 2.77–2.72 (m, 1H), 1.72–1.59 (m, 3H), 1.57 (s, 3H), 1.50 (s, 3H), 1.36–1.27 (m, 1H), 1.23 (t, J=7.1 Hz, 3H).

EXAMPLE 8

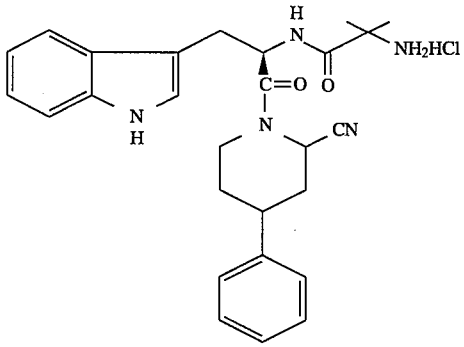

Step A: 2-Cyano- 1-hydroxy-4-phenylpiperidine

To a stirred solution of 4-phenylpiperidine (10 g, 0.062 mole) in methanol (30 mL), was added a solution of sodium tungstate dihydrate (0.82 g, 2.48 mmole) in water (7 mL). With stirring at 0°, hydrogen peroxide (30%, 13.9 mL, 0.136 mole) was added dropwise. After complete addition, the reaction mixture was stirred for an additional 3 hours, and then sodium cyanide (4.56 g, 0.093 mole) was added, followed by 4 N HCl (22 mL, 0.088 mole). The reaction mixture was stirred overnight during which time it warmed to room temperature. The solid was collected by filtration through glass sinter funnel, and the solution was neutralized to pH 7 and was extracted with dichloromethane. The organic extract was combined with the solid and dried over MgSO4 and evaporated. Flash column purification eluting with 40% ethyl acetate in hexane gave 2-cyano-1-hydroxy-4-phenylpiperidine(8.6 g).

$^1$HNMR (400 MHz, $CDCl_3$ ): 7.35–7.17 (m, 5 H), 6.01 (br. s, 1H), 4.34 (br. s, 1 H), 3.31 (td, J=3, 11 Hz, 1 H), 3.09 (dr, J=11, 3 Hz, 1 H), 2.93– 2.86 (m, 1H), 2.20–2.10 (m, 2 H), 1.97–1.80 (m, 2 H).

Step B: 2-Cyano-4-phenylpiperidine

To a stirred solution of the intermediate from the previous step (500 mg) in methanol (10 mL) at room temperature, was added $TiCl_3$ (10% solution in 20–30% hydrochloric acid (3 mL). The mixture was stirred for 15 minutes and was neutralized by addition of 3 N NaOH. The residue were extracted with dichloromethane four times and the organic extracts was combined, dried over MgSO4, and evaporated to give 450 mg of 2-cyano 4-phenylpiperidine, which was used without further purification.

Step C:

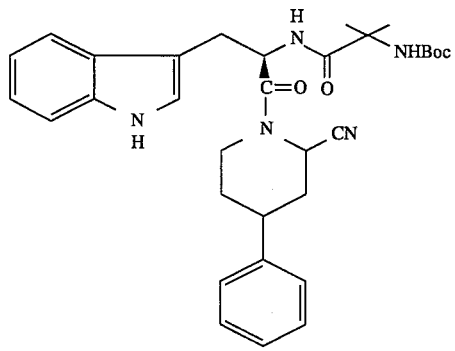

Following the procedure from Example 3, Step A, using the intermediate from the previous step, afforded two compounds after MPLC purification eluting with 60% ethyl acetate in hexane. The one which came out of the column first was designated as diastereomer 1, and the other one as diastereomer 2.

$d_1$: FAB-MS calc. for $C_{32}H_{39}N_5O_4$: 557; Found: 558 (M+H)

$d_2$: FAB-MS calc. for $C_{32}H_{39}N_5O_4$: 557; Found: 558 (M+H)

Step D:

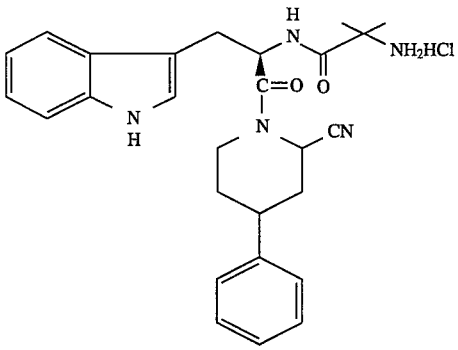

Following the experimental procedure from Example 1, Step B using products from the previous step and HCl gas in ethyl acetate at 0° C. gave the desired products.

$d_1$: FAB-MS calc. for $C_{27}H_{31}N_5O_2$: 457; Found: 458 (M+H)

$d_2$: FAB-MS calc. for $C_{27}H_{31}N_5O_2$: 457; Found: 458 (M+H)

EXAMPLE 9

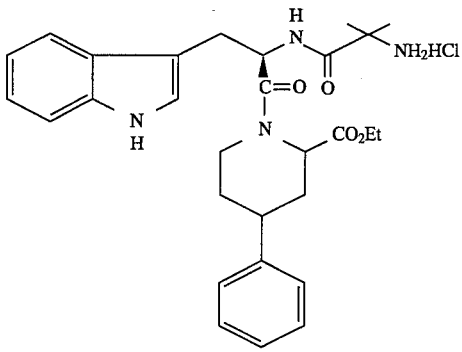

Step A: 2-Cyano-4-phenylpyridine

To a stirred solution of 4-phenylpyridine N-oxide (25 g, 0.146 mmol) in dichloromethane (200 ml) at room temperature was added trimethylsilyl cyanide (17.4 g), followed by the slow addition of dimethyl carbamyl chloride (16.2 ml) in dichloromethane (50 ml) over a 30 minute period. The reaction mixture was stirred at room temperature for one day, and then to it potassium carbonate solution (10%,150 ml) was added slowly. Stirring continued for an additional 30 minutes, the organic layer was separated, and the aqueous layer was extracted with dichloromethane. The extracts were combined and dried over magnesium sulfate. Evaporation in vacuo gave a crude reaction product (35 g) as a white solid. It was used without further purification.

FAB-MS calc. for Cb $12H8N2$: 180; Found: 181 (M+H)

1HNMR (400 MHz, CD3OD): 8.71 (dd, 1 H), 8.19 (dd, 1H), 7.94 (dd, 1 H), 7.81–7.78 (m, 2 H), 7.56–7.50 (m, 3 H).

Step B: 4-Phenylpyridine-2-carboxylic acid

A solution of the product from the previous step (25 g) in 100 ml of 6N HCl was refluxed for one day. The solution was cooled to room temperature, at which time, crystallization started to occur. The crystals were filtered and collected to give the product (27.5 g, 87%).

Step C: Ethyl 4-phenylpyridine-2-carboxylate hydrochloride

To a solution of the intermediate prepared in the previous step (5.0 g, 21.2 mmol), ethanol (2 g), DMAP (20 mg) and N-methyl morpholine (1 eq.) in dichloromethane, was added EDC (1.5 eq.). The reaction mixture was stirred at 0° C. overnight. The solution was washed with saturated sodium bicarbonate, dried over anhydrous magnesium sulfate; then filtered and concentrated. Purification by MPLC eluting with 40% ethyl acetate in hexane gave ethyl 4-phenylpyridine-2-carboxylate (3.71 g, 77%). The compound was converted to its HCl salt by treatment with HCl gas in ethyl acetate followed by evaporation.

Step D: Ethyl 4-phenylpiperidine-2-carboxylate

A suspension of the product from the previous step (200 mg) and platinum dioxide (20 mg) in ethanol was stirred under a hydrogen balloon for three hours. The reaction mixture was then filtered through celite and evaporated. The resulting material was used without further purification.

Step E:

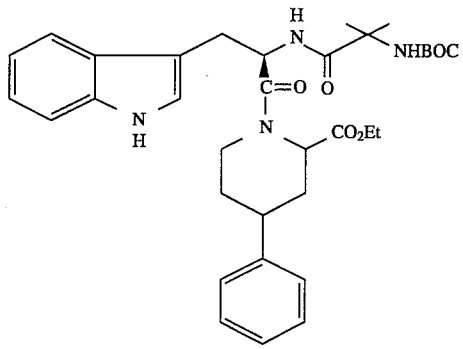

To a solution of the intermediate prepared in the previous step (200 mg ), and intermediate 1 (1 eq.), HOBT (1 eq.), and NMM (1 eq.) in dichloromethane was added EDC (1.5 eg.) at 0° C. The reaction mixture was stirred at 0° C. overnight. The solution was washed with saturated sodium chloride, dried over anydrous magnesium sulfate, filtered and then concentrated. Purification by MPLC eluting with 50% ethyl acetate in hexane provided the compound as a diastereomeric mixture.

Step F:

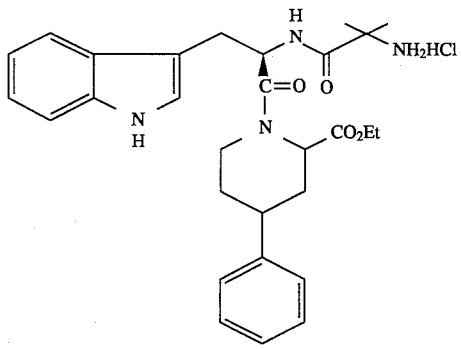

To a stirred solution of the intermediate from the previous step (30 mg) in ethyl acetate (2 mL) at 0° C., was bubbled HCl gas until it was saturated. The reaction mixture was stirred for 15 minutes and was evaporated to dryness to give the product.

FAB-MS calc. for $C_{29}H_{36}N_4O_4$: 504; Found 505 (M+H)

The additional Products shown in Table I were prepared according to Example 9 Steps E and F, using Intermediate 2 or Intermediate 3 and the intermediate from step D.

TABLE I
ADDITIONAL EXAMPLES

| entry | $R_1$ | Product MF FAB-MS (M + 1) |
|---|---|---|
| 1 | $Ph(CH_2)_3-$ | $C_{29}H_{39}N_3O_4$ 494 |
| 2 | $PhCH_2OCH_2-$ | $C_{28}H_{37}N_3O_5$ 496 |

Likewise the compounds shown below are prepared according to Example 9 by introduction of the 2-cyano substitutent to a variety of readily available substituted 4-phenylpyridines with separation of isomers where necessary, followed by hydrolysis, reestrification with anhydrous acidic ethanol and hydrogenation of the pyridine ring to prepare the following intermediates:

which may be reacted with Intermediate 1 or 3 to give the following compounds respectively.

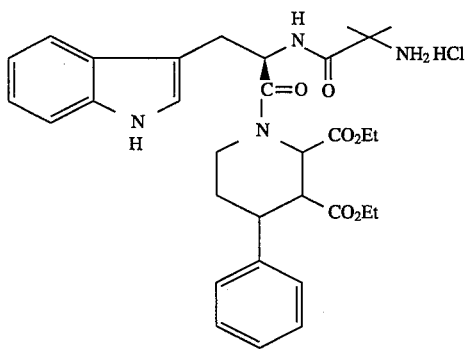

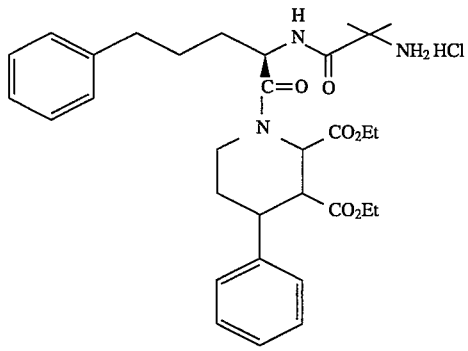

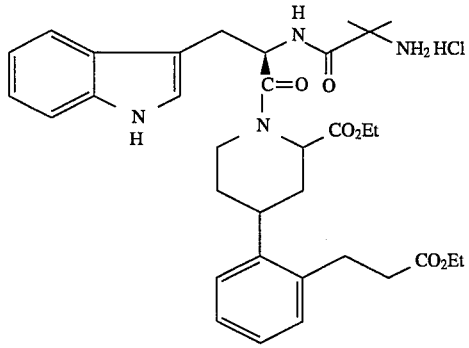

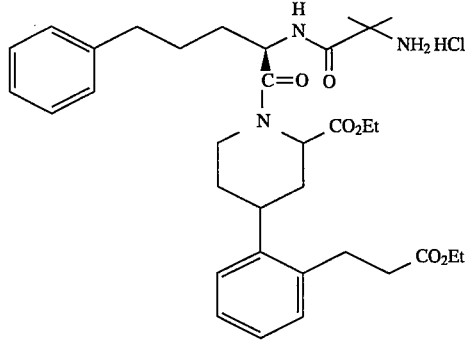

-continued

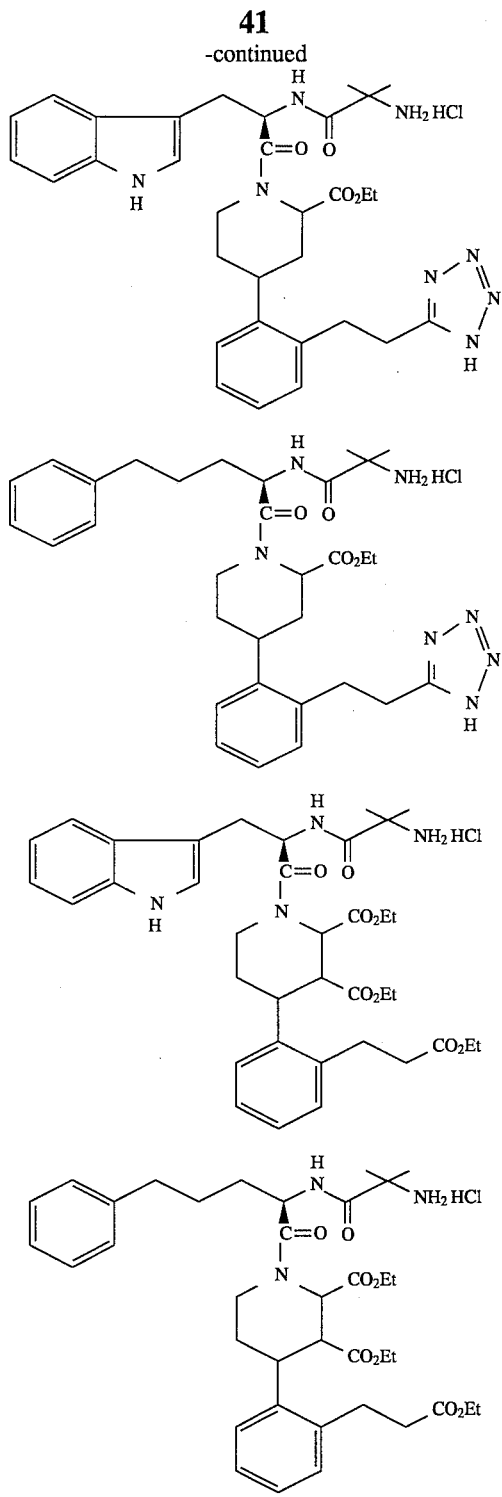

EXAMPLE 10

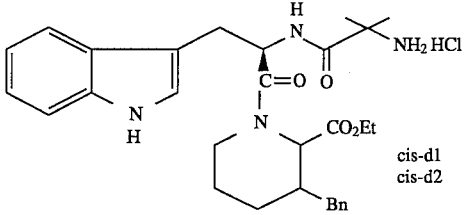

cis-d1
cis-d2

Step A: 3-Benzylpyridine N-oxide

A solution of 3-benzylpyridine (25 g, 0.148 tool) in hydrogen peroxide (30%, 15.1 mL) and acetic acid (100 mL) was refluxed for one day. Then more hydrogen peroxide (3 mL) was added and the resulting mixture was refluxed overnight. The reaction mixture was then evaporated and partitioned between a mixture of 3 N HCl, brine and dichloromethane. The organic layer was separated, dried and evaporated to give the desired compound (27.6 g, 100%).

Step B: 3-Benzyl-2-cyanopyridine

Prepared according to the procedure in Example 9 step A from the intermediate from the previous step (27 g). The crude reaction product was purified by a SiO2 flash column eluting with 20–40% ethyl acetate in hexane to give 5-benzyl-2-cyanopyridine (3.0g, 10%) and 3-benzyl-2-cyanopyridine (24.2 g, 85%).

Step C: 3-Benzylpyridine-2-carboxylic acid hydrochloride

A solution of 3-benzyl-2-cyanopyridine (19.1 g) in concentrated hydrochloric acid (50 mL) and water (50 mL) was refluxed for two days. The resulting solution was evaporated to give a solid (30.1 g 100%, which contains an equal molar amount of ammonium chloride).

Step D: Ethyl 3-benzylpyridine-2-carboxylate hydrochloride

Thionyl chloride (15.2 g) was carefully dissolved in ethanol (300 mL) and the resulting solution was added to the intermediate from the previous step (20 g). The mixture was refluxed overnight and then evaporated to give the crude product as hydrochloride salt. The crude product was dissolved in dichloromethane and washed with saturated sodium bicarbonate. The organic solution was dried, evaporated and purified with a short SiO2 column to give the product as free base (18.2 g). To a solution of this intermediate (16.5 g) in ethyl acetate (80 mL), was bubbled HCl gas until it was saturated. The mixture was then s evaporated to give the HCl salt (18.9 g).

Step E: Ethyl 3-benzylpiperidine-2-carboxylate hydrochloride

A suspension of the product from the previous step (1.0 g) and platinum dioxide (100 mg) in ethanol was stirred under

Step F:

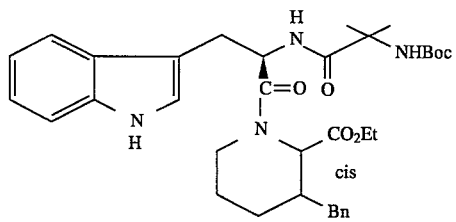

To a solution of the intermediate prepared in the previous step (180 mg, 0.634 mmol), and intermediate 1 (1 eq.), HOBT (1 eq.) and NMM (1 eq.) in dichloromethane, was added EDC (1.5 eq.) at 0° C. The reaction mixture was stirred at 0° C. overnight. The solution was washed with saturated sodium chloride, dried over anydrous magnesium sulfate; then filtered and concentrated. Purification by MPLC eluting with 50% ethyl acetate in hexane provided two enantiomerically pure compounds. The compound which came out first from the column was designated as d1 (146 mg); and the compound which came out of the column second was designated as d2 (141 g).

d1 FAB-MS calc. for $C_{35}H_{46}N_4O_6$: 618; Found 618 (M+H)

d2 FAB-MS calc. for $C_{35}H_{46}N_4O_6$: 618; Found 619 (M+H)

Step G:

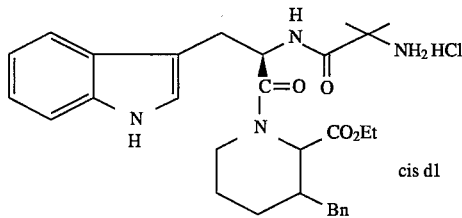

To a stirred solution of the intermediate dl from the previous step (130 mg) in ethyl acetate (2 mL) at 0° C., was bubbled HCl gas until it was saturated. The reaction mixture was stirred for 15 minutes and it was evaporated to dryness to give the product (111 mg, 95%)

FAB-MS calc. for $C_{30}H_{38}N_4O_4$: 518; Found 519 (M+H)

Step H:

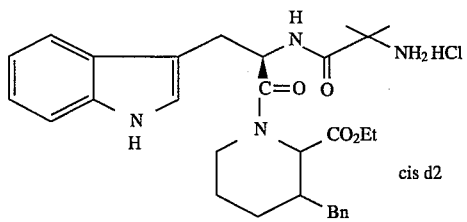

The compound was prepared according to the procedure of the previous step from the intermediate d2 from Step F (130 mg). Product: 114 mg, 98 %

FAB-MS calc. for $C_{30}H_{38}N_4O_4$: 518; Found 519 (M+H)

The additional products shown in Table II were prepared according to Example 10 Steps F and G, using Intermediate 2 or Intermediate 3 and the intermediate from step E. No separation of the diastereoisomers was observed during MPLC purification of the Boc precursor.

TABLE II

ADDITIONAL EXAMPLES

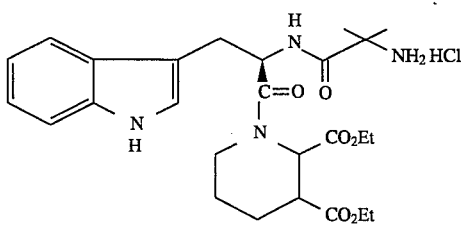

| entry | $R_1$ | Product MF FAB-MS (M + 1) |
|---|---|---|
| 1 | $Ph(CH_2)_3-$ | $C_{30}H_{41}N_3O_4$ 508 |
| 2 | $PhCH_2OCH_2-$ | $C_{29}H_{39}N_3O_5$ 510 |

EXAMPLE 11

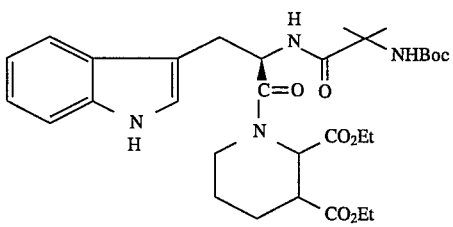

Step A: Diethyl piperidine-2,3-(cis)-dicarboxylate

Hydrogen chloride gas was bubbled into ethanol (400 mL) until 22 g was absorbed. Pyridine-2,3-dicarboxylic acid (100 g) was dissolved in this solution and the resulting mixture was refluxed overnight. The reaction mixture was divided into two portions and each was shaken with PtO2 (1.4 g) in Parr shakers under 40 psi of hydrogen for 8 hours. The reaction mixture was combined and filtered through celite and washed with plenty of ethanol. Evaporation gave a gray solid which was washed with ethyl acetate to give a white solid after filtration (74.8 g)

Step B:

The compound was prepared according to the procedure of Example 1 Step A from the intermediate from the previous step (178 mg) and Intermediate 1. Product: 234 mg FAB-MS calc. for $C_{31}H_{44}N_4O_8$: 600; Found 601(M+H)

Step C:

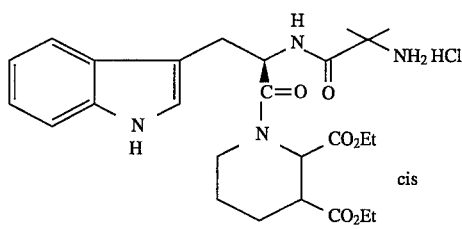

cis

The compound was prepared according to the procedure of Example 1 Step B from the intermediate from the previous step (230 mg). Product: 215 mg FAB-MS calc. for $C_{26}H_{36}N_4O_6$: 500; Found 501 (M+H), 523 (M+Na)

The additional intermediates shown in Table III were prepared from the corresponding pyridine analogs according to the above established procedures from the corresponding pyridine derivatives as exemplified in Example 11 step A and the final products were prepared according to Steps B and C

TABLE III
ADDITIONAL EXAMPLES

| entry | Intermediate (QH)<br>MF<br>FAB-MS (M + 1) | Product<br>MF<br>FAB-MS (M + 1) |
|---|---|---|
| 1 | ![piperidine with CH3, CO2Et] H-N, CH3, CO2Et | $C_{24}H_{34}N_4O_4$<br>443<br>diastereomeric mixture |
| 2 | H-N, CH3, CO2Et, CH3 | $C_{25}H_{36}N_4O_4$<br>457<br>diastereomeric mixture |
| 3[a] | H-N, CH3, ""CO2Et, CH3 | $C_{25}H_{36}N_4O_4$<br>457<br>diastereomeric mixture |

[a]The intermediate was prepared by epimerization of its all cis isomer with KHMDS in THF.

[a]:The intermediate was prepared by epimerization of its all cis isomer with KHMDS in THF.

EXAMPLE 12

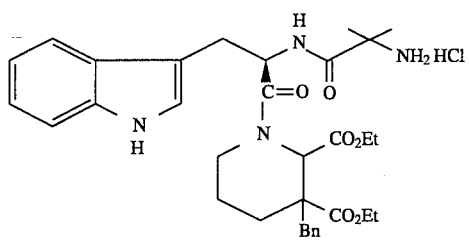

Step A: Diethyl N-Boc-piperidine-(cis)-2,3-dicarboxylate

To a stirred solution of the intermediate from Example 11 Step A (10 g, 37.6 mmol) and trimethylamine (6.4 mL) in dichloromethane (50 mL), was added di-t-butyl dicarbonate (10.7 g) and the resulting mixture was stirred at room temperature overnight. The reaction mixture was diluted with dichloromethane and was washed with a mixture of 3 N HCl and brine. The organic layer was dried, evaporated and purified with a silica gel column eluting with a gradient of 10–30% ethyl acetate in hexane to give the desired compound (9.61 g).

Step B:

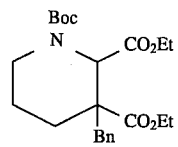

To a stirred solution of KHMDS (3.79, 19 mmol) in THF (150 mL) at –78° C. under argon was added a solution of diethyl N-Boc-piperidine-(cis)-2,3-dicarboxylate (5 g, 15.2 mmol) over a 30 minute period. The solution was allowed to stir an additional 30 minutes at –78° C.; then benzyl bromide (2.73 g, 15.9 mmol) was added slowly to the solution. The reaction mixture was stirred overnight and allowed to warm to room temperature. The material was concentrated, then diluted with water, and extracted with ethyl acetate (100 mL). The organic layer was dried over anhydrous magnesium sulfate, filtered, and concentrated. Purification by silica gel flash column chromatography, eluting with 20% ethyl acetate in hexane provided two diastereoisomers. The compound which came out first from the column was designated as d1 (1.01 g); and the compound which came out of the column second was designated as d2 (3.75 g). NMR established the esters are trans in d1 and cis in $d_2$.

Step C:

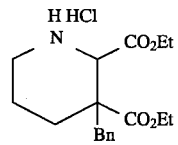

The compounds were prepared according to the procedure of Example 1 Step B from the intermediates from the previous step. Intermediate d1 (850 mg) yielded the $d_1$ title compound (711 mg, 98%). Intermediate d2 (3.2 g) yielded the $d_2$ title compound (2.58 g, 96%)

d1 FAB-MS calc. for $C_{18}H_{25}NO_4$: 319; Found 320(M+H)

d2 FAB-MS calc. for $C_{18}H_{25}NO_4$:319; Found 320(M+H)

Step D:

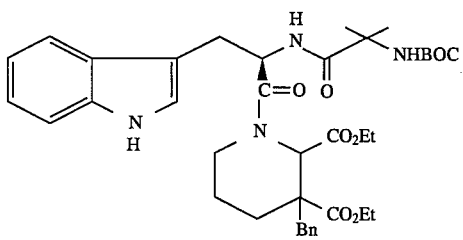

The compounds were prepared according to the procedure of Example 1 Step A from the intermediates from the previous step. Intermediate d1 (228 mg) yielded a mixture of trans diastereomers (128 mg, 30%).

Intermediate d2 (228 mg) yielded a mixture of cis diastereomers (164 mg, 30%).

Step E:

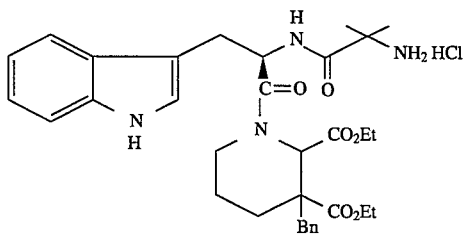

The compounds were prepared according to the procedure of Example 1 Step B from the intermediates from the previous step. Intermediate d1 (120 mg) yielded the title compound as mixture of trans ($d_1$) diastereomers (106 mg, 97%).

Intermediate d2 (155 mg) yielded the title compound as mixture of cis (d2) diastereomers (135 mg, 96%).

d1 FAB-MS calc. for $C_{33}H_{42}N_4O_6$: 590; Found 591(M+H)

d2 FAB-MS calc. for $C_{33}H_{42}N_4O_6$: 590; Found 591 (M+H)

The additional intermediates shown in Table IV were prepared according to the above established procedures using N-Boc intermediates from Table III as exemplified in Example 12 Steps A, B and C and the final products were prepared according to Steps D and E.

TABLE IV

ADDITIONAL EXAMPLES

| entry | Intermediate (QH) MF FAB-MS (M + 1) | Product MF FAB-MS (M + 1) |
|---|---|---|
| 1 | H-N, CH3, CO2Et, Bn | d1: $C_{31}H_{40}N_4O_4$ 533 |
| 2 | H-N, CH3, CO2Et, Bn | d2: $C_{31}H_{40}N_4O_4$ 533 |
| 3 | H-N, CH3, CO2Et, Bn, CH3 | mixture of diastereomers $C_{32}H_{42}N_4O_4$ 547 |

Likewise the compounds shown below are prepared according to Example 12 by alkylating with 2-picolyl chloride or 4-bromomethylthiazole to give the following intermediates:

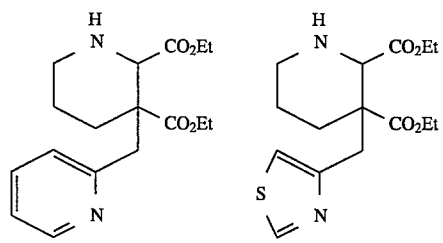

which may then be reacted with Intermediates 1 or 2 to give the following compounds respectively:

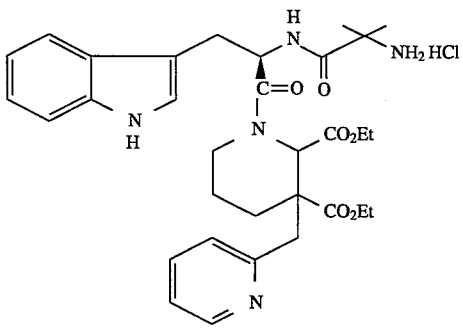

49
-continued

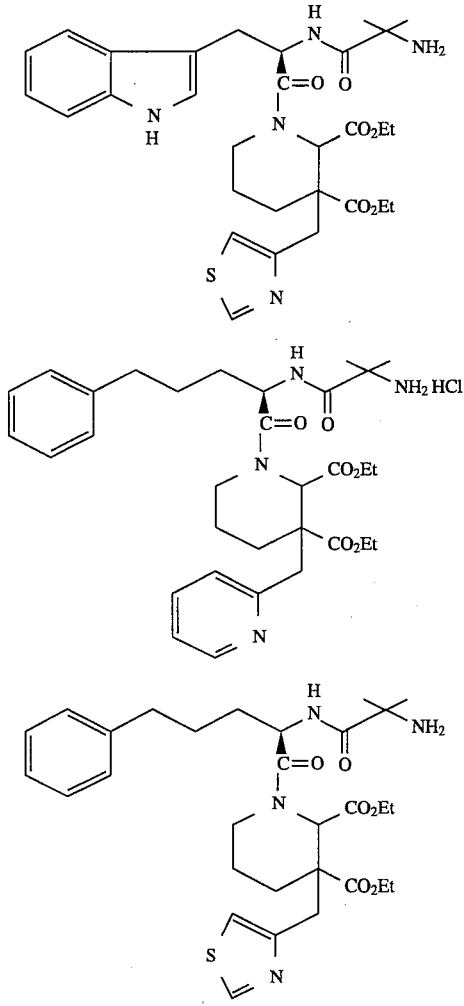

EXAMPLE 13

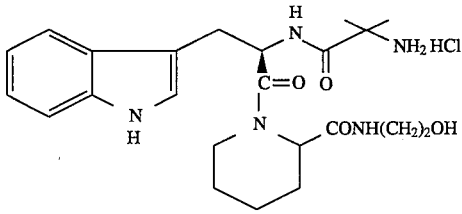

Step A:

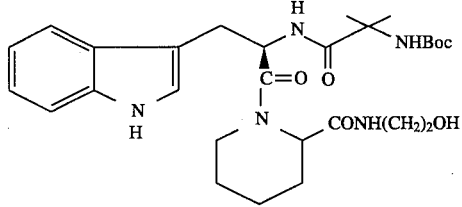

To a stirred solution of dl-2-pipecolamidoethanol (100 mg, (1.16 mmol), HOBT (78.38 mg, 1.16 mmol) and Intermediate 1 (226.12 mg, 1.16 mmol) in dichloromethane (3ml) at ambient temperature was added 4-methyl morpholine (63.8 ml, (1.16 mmol). The mixture was cooled to 0° C. and to which was added EDC (222.3 mg, 2.32 mmol). The reaction mixture was stirred at room temperature for 16 h. After evaporation, the residue was partitioned in ethyl acetate and 1N hydrochloric acid. The organic layer was washed with saturated sodium bicarbonate, brine, dried over magnesium sulfate, filtered, and evaporated to an oily foam which was purified by preparative tlc (acetone/chloroform: 3/7) to give 91 mg of the product ($R_f$=0.45).

CI-MS: calc. for $C_{28}H_{41}N_5O_6$: 543; Found 544(M+H)

$^1$H NMR (400 MHz, CDCl$_3$): δ8.35 (br.s, 1H), 7.57 & 7.55 (2s, H),7.35, 7.33, (2s, 2H), 7.17 (t, J=6.95Hz, 1H), 7.15–7.07 (m, 3H), 7.03 (distorted t, J=4.95 Hz, 1H), 5.16 (d, J=4.68 Hz, 1H), 4.94 (m, 2H), 3.65 (m, 2H), 3.55–3.10 (m, 5H), 2.9–2.62 (m, 4H), 2.3–2.2 (m, 1H), 1.43, 1.46 and 1.41 (3 s, total 15H), 1.00 (m, 1H), 0.83 (m, 1H).

Step B:

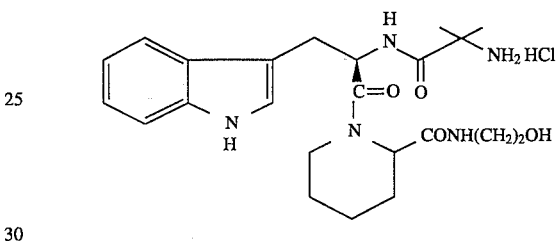

Prepared according to the experimental procedure from Example 1 Step B using product from the previous step and HCl gas in ethyl acetate at 0° C.

CI-MS :calc. for $C_{23}H_{33}N_5O_4$: 443; Found 444(M+H)

$^1$H NMR (400 MHz, CD$_3$OD): δ7.54 (d, J=7.7 Hz, 1H), 7.36 (d, J=8.1 Hz), 7.12 (distorted t, J=7.5 Hz, 1H), 7.03 (distorted t, J=7.5Hz, 1H), 4.97–4.92 (m, 1H), 3.63 (m, 1H), 3.75 (br. d, 1H), 2.82 (br. t, J=2.3 Hz, H), 2.07 (br. d, J=2.3 Hz, 1H), 1.66–1.57 (m, 6H), 1.55–0.88 (m, 4H), 0.70–0.55 (m, 1H).

The additional compounds shown in Table V were prepared according to Steps A and B using Intermediate 1. The piperidine intermediates were either commercially available or were prepared according to the above established procedures or from literature procedures.

TABLE V

ADDITIONAL EXAMPLES

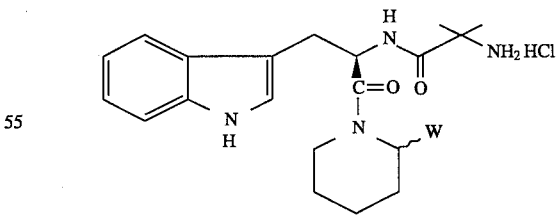

Product

| | W | MF | FAB (or CI)-MS (M + 1) |
|---|---|---|---|
| 1 | —CO$_2$CH$_3$ | C$_{22}$H$_{30}$N$_4$ | 415 |
| 2 | —CONH(CH$_2$)$_2$OH | C$_{23}$H$_{33}$N$_5$O$_4$ | 444 |
| 3 | —CONHCH$_2$C(CH$_3$)$_2$OH | C$_{25}$H$_{37}$N$_5$O$_4$ | 472 |
| 4 | —CONHCH$_2$CH(OH)CH$_3$ | C$_{24}$H$_{35}$N$_5$O$_4$ | 458 |

TABLE V-continued

ADDITIONAL EXAMPLES

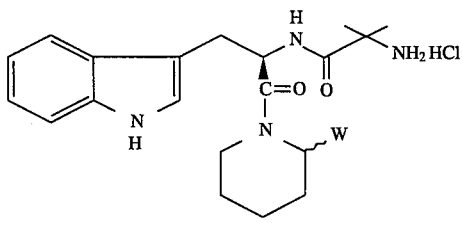

Product

| W | MF | FAB (or CI)-MS (M + 1) |
|---|---|---|
| 5 | $-CO_2NH_2$ | $C_{21}H_{29}N_5O_3$ | 399 (EI, M$^+$) |
| 6 | $-CH_2COCH_3$ | $C_{23}H_{32}N_3O_4$ | 413 |
| 7 | $-CH(OH)Ph-p-Cl$ | $C_{27}H_{33}N_4O_3Cl$ | 497 |
| 8 | $-CH(OH)CH_2CH_3$ | $C_{23}H_{34}N_4O_3$ | 415 |
| 9 | $-CONHBn$ | $C_{28}H_{35}N_5O_3$ | 490 |
| 10 | $-CONH(CH_2)_2CH_3$ | $C_{24}H_{35}N_5O_3$ | 442 |
| 11 | (structure) | $C_{25}H_{37}N_5O_3$ | 456 |
| 12 | $-CONHPh$ | $C_{27}H_{33}N_5O_3$ | 476 |
| 13 | (tetrazole structure) | $C_{21}H_{28}N_8O_2$ | 425 |
| 14 | (oxadiazole structure) | $C_{23}H_{30}N_6O_3$ | 439 |

The additional compounds shown in Table Va were prepared according to Steps A and B using Intermediate 3 and some of intermediates used in the previous table.

TABLE Va

ADDITIONAL EXAMPLES

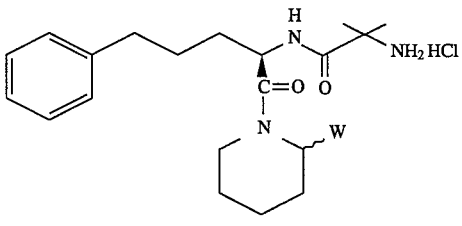

Product

| W | MF | FAB (or CI)-MS (M + 1) |
|---|---|---|
| 1 | $-CO_2CH_2CH_3$ | $C_{23}H_{35}N_3O_4$ | 418 |
| 2 | $-CONHCH_2C(CH_3)_2OH$ | $C_{25}H_{40}N_4O_4$ | 461 |
| 3 | $-CONH(CH_3)_2$ | $C_{23}H_{33}N_5O_3$ | 428 |
| 4 | $-CH(OH)Ph-p-Cl$ | $C_{27}H_{36}N_3O_3Cl$ | 486 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical careers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula:

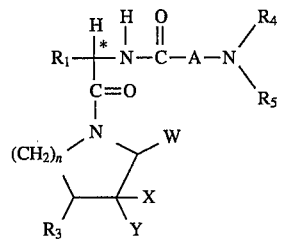

wherein:

$R_1$ is selected from the group consisting of: $C_1$–$C_{10}$ alkyl, aryl, aryl($C_1$–$C_6$ alkyl), ($C_3$–$C_7$ cycloalkyl)($C_1$–$C_6$ alkyl)—, ($C_1$–$C_5$ alkyl)-K-($C_1$–$C_5$ alkyl)—, aryl($C_0$–$C_5$ alkyl)-K-($C_1$–$C_5$ alkyl)—, and ($C_3$—$C_7$ cycloalkyl)($C_0$–$C_5$ alkyl)-K-($C_1$–$C_5$ alkyl)—, where K is O, $S(O)_m$, $N(R_2)C(O)$, $C(O)N(R_2)$, $OC(O)$, $C(O)O$, $-CR_2=CR_2-$, or $-C\equiv C-$, where aryl is selected from: phenyl, naphthyl, indolyl, azaindole, pyridyl, benzothienyl, benzofuranyl, thiazolyl, and benzimidazolyl, and $R_2$ and alkyl may be further substituted by 1 to 9 halogen, $S(O)_mR_{2a}$, 1 to 3 of $OR_{2a}$ or $C(O)OR_{2a}$, and aryl may be further substituted by 1 to 3 of $C_1$–$C_6$ alkyl, 1 to 3 of halogen, 1 to 2 of $OR_2$, methylenedioxy, $-S(O)_mR_2$, 1 to 2 of $-CF_3$, $-OCF_3$, nitro, $-N(R_2)C(O)(R_2)$, $-C(O)OR_2$, $-C(O)N(R_2)(R_2)$, -1H-tetrazol-5-yl, $-SO_2N(R_2)(R_2)$, $-N(R_2)SO_2$ phenyl, or $-N(R_2)SO_2R_2$;

$R_2$ is selected from: hydrogen, $C_1$–$C_6$ alkyl, and $C_3$–$C_7$ cycloalkyl, and where two $C_1$–$C_6$ alkyl groups are present on one atom, they may be optionally joined to form a $C_3$–$C_8$ cyclic ring.

$R_3$ is selected from: hydrogen, $-(CH_2)_r$phenyl, $-(CH_2)_r$naphthyl, $-C_1$–$C_{10}$ alkyl, $-C_3$–$C_7$ cycloalkyl, where the phenyl, naphthyl and $C_3$–$C_7$ cycloalkyl rings may be substituted by 1 to 3 substituents selected from the group consisting of: $C_1$–$C_6$ alkyl, halogen, $-OR_2$, $-NHSO_2CF_3$, $-(CH_2)_rOR_6$, $-(CH_2)_rN(R_2)(R_6)$, $-(CH_2)_r(R_6)$, $-(CH_2)_rC(O)OR_2$, $-(CH_2)_rC(O)OR_6$, $-(CH_2)_rOC(O)R_2$, $-(CH_2)_rOC(O)R_6$, $-(CH_2)_rC(O)R_2$, $-(CH_2)_rC(O)R_6$, $-(CH_2)_rC(O)N(R_2)(R_2)$, $-(CH_2)_rC(O)N(R_2)(R_6)$, $-(CH_2)_rN(R_2)C(O)R_2$, $-(CH_2)_rN(R_2)C(O)R_6$, $-(CH_2)_rN(R_6)C(O)R_2$, $-(CH_2)_rN(R_6)C(O)R_6$, —(CH₂)ᵣN(R₂)C(O) OR₂, —(CH₂)ᵣN(R₂)C(O)OR₆,
—(CH₂)ᵣN(R₆)C(O)OR₂, —(CH₂)ᵣN(R₆)C(O)OR₆,
—(CH₂)ᵣN(R₂)C(O)N(R₂)(R₆),
—(CH₂)ᵣN(R₂)C(O)N(R₂)(R₂),
—(CH₂)ᵣN(R₆)C(O)N(R₂)(R₆), (CH₂)ᵣN(R₂)SO₂R₆,
—(CH₂)ᵣN(R₂)SO₂R₂, —(CH₂)ᵣN (R₆)SO₂R₂,
CH₂)ᵣN(R₆)SO₂R₆, —(CH₂)ᵣOC(O)N(R₂)(R₆),
—(CH₂)ᵣOC(O)N(R₂)(R₂), —(CH₂)ᵣSO₂ N(R₂)(R₆),
—(CH₂)ᵣSO₂N(R₂)(R₂),(CH₂)ᵣSO₂NHC(O)R₆,—
(CH₂)ᵣSO₂NHC (O)R₂, —(CH₂)ᵣSO₂NHC(O)OR₆,
—(CH₂)ᵣSO₂NHC(O)OR₂,
—(CH₂)ᵣC(O)NHC(O)NR₂,
—(CH₂)ᵣC(O)NHC(O)NR₆,
—(CH₂)ᵣC(O)NHC(O)R₂, —(CH₂)ᵣCONHC(O)R₆,
—(CH₂)ᵣCONHSO₂R₆,—(CH₂)ᵣCONHSO₂R₂,
—(CH₂)ᵣCONHSO₂N (R₂ )R₂), —(CH₂)ᵣCONHSO₂N
(R₂)R₆), —(CH₂)ᵣN(R₂)SO₂N(R₂)R₆),
—(CH₂)ᵣN(R₆)SO₂N(R₂)R₆), —(CH₂)ᵣS(O)ₘR₆, and
—(CH₂)ᵣS(O)ₘR₂;

W is selected from the group consisting of: —CN,
—C(O)OR₈, —C(O)OR₂, —C(O)O(CH₂)₁aryl,
—C(O)N(R₂)(R₂); —C(O)N(R₂)(R₈),
—C(O)N(R₂)(CH₂)₁aryl, —CH₂N(R₂)C(O)R₈
—CH₂N(R₂)C(O)(CH₂)₁aryl, —(CH₂)ᵣOR₂,
—CH(OH)R₂, —CH(OH)(CH₂)₁aryl, —C(O)R₂,
—C(O)(CH₂)₁aryl, 1H-tetrazol-5-yl, 5-amino-1,2,4-oxadiazol-3-yl, and 5-methyl-1,2,4-oxadiazol-3-yl, where R₈ is hydrogen, C₁-C₆ alkyl, or C₁-C₆ alkyl substituted by OR₂, C(O)OR₂, CON(R₂)(R₂), N(R₂)C(O)R₂, N(R₂)C(O)N(R₂)(R₂), and aryl is phenyl, pyridyl, or 1H-tetrazol-5-yl;

X is selected from: hydrogen, -C≡N,
—(CH₂)qN(R₂)C(O)R₂,
—(CH₂)qN(R₂)C(O)(CH₂)ₜaryl,
—(CH₂)qN(R₂)SO₂(CH₂)ₜaryl, —(CH₂)qN(R₂)SO₂R₂,
—(CH₂)qN(R₂)C(O)N(R₂)(CH₂)ₜaryl,
—(CH₂)qN(R₂)C(O)N(R₂)(R₂),
—(CH₂)qC(O)N(R₂)(R₂),
—(CH₂)qC(O)N(R₂)(CH₂)ₜaryl, —(CH₂)qC(O)OR₂,
—(CH₂)qC(O)O(CH₂)ₜaryl, —(CH₂)qOR₂,
—(CH₂)qOC(O)R₂, —(CH₂)qOC(O)(CH₂)ₜaryl,
—(CH₂)qOC(O)N(R₂)(CH₂)ₜaryl,
—(CH₂)qOC(O)N(R₂)(R₂), —(CH₂)qC(O)R₂,
—(CH₂)qC(O)(CH₂)ₜaryl, —(CH₂)qN(R₂)C(O)OR₂,
—(CH₂)qN(R₂)SO₂N(R₂)(R₂), —(CH₂)qS(O)ₘR₂, and
—(CH₂)qS(O)ₘ(CH₂)ₜaryl, where an R₂, (CH₂)q and (CH₂)ₜ group may be optionally substituted by 1 to 2 C₁-C₄ alkyl, hydroxyl, C₁-C₄ lower alkoxy, carboxyl, CONH₂, S(O)ₘCH₃, carboxylate C₁-C₄ alkyl esters, or 1H-tetrazol-5-yl, and aryl is phenyl, naphthyl, pyridyl, thiazolyl, or 1H-tetrazol-5-yl groups which may be optionally substituted by 1 to 3 halogen, 1 to 3 —OR₂, —CON(R₂)(R₂), —C(O)OR₂, 1 to 3 C₁-C₄ alkyl, —S(O)ₘR₂, or 1H-tetrazol-5-yl;

Y is selected from: hydrogen, C₁-C₁₀ alkyl, —(CH₂)ₜaryl, —(CH₂)q(C₃-C₇ cycloalkyl), —(CH₂)q-K-(C₁-C₆ alkyl), —(CH₂)q-K-(CH₂)ₜaryl, —(CH₂)q-K-(CH₂)ₜ(C₃-C₇ cycloalkyl containing O, NR₂, S), and —(CH₂)q-K-(CH₂)ₜ(C₃-C₇ cycloalkyl), where K is O, S(O)ₘ, C(O)NR₂, CH=CH, C≡C, N(R₂)C(O), C(O)NR₂, C(O)O, or OC(O), and where the alkyl, R₂, (CH₂)q and (CH₂)ₜ groups may be optionally substituted by C₁-C₄ alkyl, hydroxyl, C₁-C₄ lower alkoxy, carboxyl, —CONH₂ or carboxylate C₁-C₄ alkyl esters, and aryl is phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrrazinyl, or isothiazolyl which is optionally substituted by 1 to 3 halogen, 1 to 3 —OR₂,—C(O)OR₂,—C(O)N(R₂)(R₂), nitro, cyano, benzyl, 1 to 3 C₁-C₄ alkyl, —S(O)ₘR₂, or 1H-tetrazol-5-yl;

R₄ and R₅ are independently hydrogen, C₁-C₆ alkyl, substituted C₁-C₆ alkyl where the substituents may be 1 to 5 halo, 1 to 3 hydroxy, 1 to 3 C₁-C₁₀ alkanoyloxy, 1 to 3 C₁-C₆ alkoxy, phenyl, phenoxy, 2-furyl, C₁-C₆ alkoxycarbonyl, S(O)ₘ(C₁-C₆ alkyl); or R₄ and R₅ can be taken together to form —(CH₂)dLa(CH₂)e— where La is C(R₂)₂, O, S(O)ₘ or N(R₂), d and e are independently 1 to 3 and R₂ is as defined above;

A is:

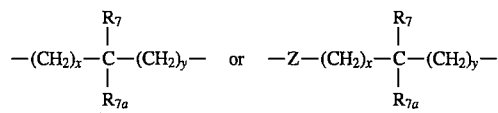

where x and y are independently 0, 1, 2 or 3;

Z is N —R₆ₐ or O, where R₆ₐ is hydrogen or C₁-C₆ alkyl;

R₆ is hydrogen, C₁-C₆ alkyl, or (CH₂)ᵥaryl, wherein the alkyl and (CH₂)ᵥ groups may be optionally substituted by 1–20(R₂), S(O)ₘR₂, 1H-tetrazol-5-yl, C(O)OR₂, C(O)N(R₂)(R₂) or SO₂N(R₂)(R₂), N(R₂)C(O)N(R₂)(R₂),and wherein aryl is phenyl, pyridyl, 1H-tetrazol-5-yl, triazolyl, imidazolyl, thiazolyl, pyrazolyl, thiadiazolyl, imidazolone-1-yl, benzimidazol-2-yl, triazolinone-yl optionally substituted with C₁-C₆ alkyl, C₃-C₆ cycloalkyl, amino, or hydroxyl;

R₇ and R₇ₐ are independently hydrogen, C₁-C₆ alkyl, trifluoromethyl, phenyl, substituted C₁-C₆ alkyl where the substituents are imidazolyl, phenyl, indolyl, p-hydroxyphenyl, OR₂, S(O)ₘR₂, C(O)O(C₁-C₆ alkyl), C₃-C₇ cycloalkyl, N(R₂)(R₂), C(O)N(R₂)(R₂); or R₇ and R₇ₐ can independently be joined to one or both of R₄ and R₅ groups to form an alkylene bridge between the terminal nitrogen and the alkyl portion of the R₇ or R₇ₐ groups, wherein the bridge contains 1 to 5 carbons atoms; or R₇ and R₇ₐ can be joined to one another to form a C₃-C₇ cycloalkyl;

l is 0, 1 or 2;

m is 0, 1, or 2;

n is 2;

q is 0, 1, 2, 3, or 4;

r is 0, 1, 2, or 3;

t is 0, 1, 2, or 3;

v is 0, 1, or 2;

and pharmaceutically acceptable salts and individual diastereomers thereof.

2. The compound of claim 1 wherein:

R₁ is selected from the group consisting of: C₁-C₁₀ alkyl, aryl (C₁-C₄ alkyl)-, C₃-C₆ cycloalkyl (C₁-C₄ alkyl)-, (C₁-C₄ alkyl)-K-(C₁-C₂ alkyl)-, aryl (C₀-C₂ alkyl)-K-(C₁-C₂ alkyl)-, and (C₃-C₇ cycloalkyl)(C₀-C₂ alkyl)-K-(C₁-C₂ alkyl)-, where K is O, S(O)ₘ, OC(O), C(O)O and the alkyl groups may be further substituted by 1 to 7 halogen, S(O)ₘR₂, 1 to 3 OR₂ or C(O)OR₂ and aryl is phenyl, naphthyl, indolyl, pyridyl, benzothienyl, or benzofuranyl which may be further substituted by 1–2 C₁-C₄ alkyl, 1 to 2 halogen, 1 to 2 OR₂, S(O)ₘR₂ or C(O)OR₂;

R₂ is hydrogen, C₁-C₆ alkyl, or C₃-C₇ cycloalkyl and where two C₁-C₆ alkyl groups are present on one atom they may be optionally joined to form a $C_4$-$C_7$ cyclic ring;

$R_3$ is hydrogen or phenyl optionally substituted in the ortho position by a $C_1$-$C_6$ alkyl group, —NHSO$_2$CF$_3$, —(CH$_2$)$_r$(1H-tetrazol-5-yl), —(CH$_2$)$_r$C(O)OR$_2$, (CH$_2$)$_r$C(O)N(R$_2$)(R$_6$);

W is -CN, —C(O)OR$_2$, —C(O)N(R$_2$)(R$_2$), —C(O)N(R$_2$)(CH$_2$)$_l$phenyl, 1H-tetrazol-5-yl, or —(CH$_2$)$_r$OR$_2$;

X is hydrogen, —(CH$_2$)$_q$C(O)N(R$_2$)(R$_6$), or —(CH$_2$)$_q$C(O)OR$_2$;

Y is hydrogen, $C_1$-$C_8$ alkyl, —(CH$_2$)$_t$phenyl, —(CH$_2$)$_t$pyridyl, or —(CH$_2$)$_t$thiazolyl;

$R_4$ and $R_5$ are independently hydrogen, $C_1$-$C_6$ alkyl, or substituted $C_1$-$C_6$ alkyl where the substituents may be 1 to 5 halo, 1 to 3 hydroxyl, S(O)$_m$($C_1$-$C_6$ alkyl) or phenyl;

$R_6$ is hydrogen, or $C_1$-$C_6$ alkyl;

A is:

$$\begin{array}{c} R_7 \\ | \\ (CH_2)x-C- \\ | \\ R_{7a} \end{array}$$

where x is 0, or 1;

$R_7$ and $R_{7a}$ are independently hydrogen $C_1$-$C_6$ alkyl, trifluoromethyl, phenyl, substituted $C_1$-$C_6$ alkyl where the substituents are imidazolyl, phenyl, indolyl, p-hydroxyphenyl, OR$_2$, S(O)$_m$R$_2$, C(O)O($C_1$-$C_6$ alkyl), $C_5$-$C_7$ cycloalkyl, N(R$_2$)(R$_2$), C(O)N(R$_2$)(R$_2$); or $R_7$ and $R_{7a}$ can independently be joined to one of $R_4$ or $R_5$ to form an alkylene bridge between the terminal nitrogen and the alkyl portion of $R_7$ or $R_{7a}$ groups to form 5 or 6 membered rings; or $R_7$ and $R_{7a}$ can be joined to one another to form a $C_3$ cycloalkyl;

l is 0 or 1;

n is 2;

m is 0, 1, or 2;

r is 0, 1, 2 or 3;

q is 0 or 1 t is 0 or 1;

and pharmaceutically acceptable salts and individual diastereomers thereof.

3. The stereospecifically defined compound of claim 1 of the formula:

[structural formula with R$_1$, R$_3$, R$_4$, R$_5$, A, W, X, Y, (CH$_2$)$_n$, C=O, N, H]

wherein $R_1$, $R_3$, $R_4$, $R_5$, A, W, X, Y, and n are as defined in claim 1.

4. A compound of the formula:

[Formula Ib - structural formula with R$_1$, R$_3$, R$_4$, R$_5$, A, W, X, Y]

wherein:

$R_1$ is selected from the group consisting of: $C_1$-$C_{10}$ alkyl, aryl ($C_1$-$C_3$ alkyl)-, and aryl ($C_0$-$C_1$ alkyl)-K-($C_1$-$C_2$ alkyl)-, where K is O or S(O)$_m$ and the aryl is phenyl, pyridyl, naphthyl, or indolyl which are optionally substituted by 1–2 $C_1$-$C_4$ alkyl, 1 to 2 halogen, 1 to 2 OR$_2$, S(O)$_m$ R$_2$ or C(O)OR$_2$;

$R_2$ is hydrogen, $C_1$-$C_6$ alkyl, or $C_3$-$C_7$ cycloalkyl and where two $C_1$-$C_6$ alkyl groups are present on one atom they may be optionally joined to form a $C_5$-$C_7$ cyclic ring;

$R_3$ is hydrogen or phenyl optionally substituted in the ortho position by a $C_1$-$C_3$ alkyl group, (CH$_2$)$_r$(1H-tetrazol-5-yl) or (CH$_2$)$_r$C(O)OR$_2$l W is —CN, —C(O)OR$_2$, or —C(O)N(R$_2$)R$_2$);

X is hydrogen or C(O)OR$_2$;

Y is hydrogen, benzyl, picoyl, or thiazolylmethyl;

$R_4$ and $R_5$ are independently hydrogen, $C_1$-$C_3$ alkyl, substituted $C_1$-$C_3$ alkyl where the substituents may be 1 to 2 hydroxyl;

A is $$\begin{array}{c} R_7 \\ | \\ (CH_2)x-C- \\ | \\ R_{7a} \end{array}$$

where x is 0, or 1;

$R_7$ and $R_{7a}$ are independently hydrogen or $C_1$-$C_4$ alkyl;

m is 0, 1, or 2;

r is 0, 1, or 2;

and pharmaceutically acceptable salts and individual diastereomers thereof.

5. A compound which is selected from the group consisting of:

[structural formula showing indole-containing compound with NH$_2$, CO$_2$Et groups]

57
-continued
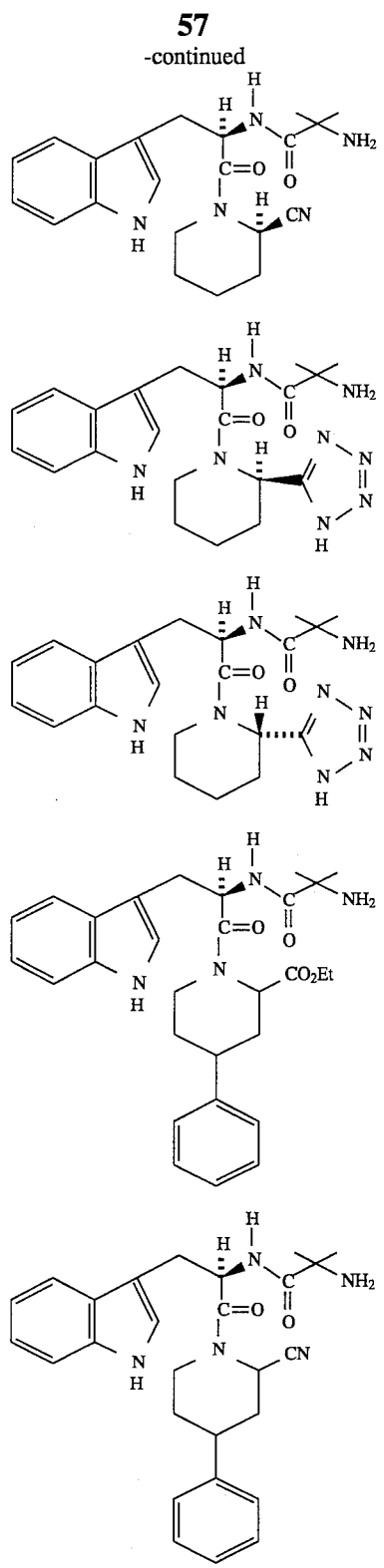
58
-continued
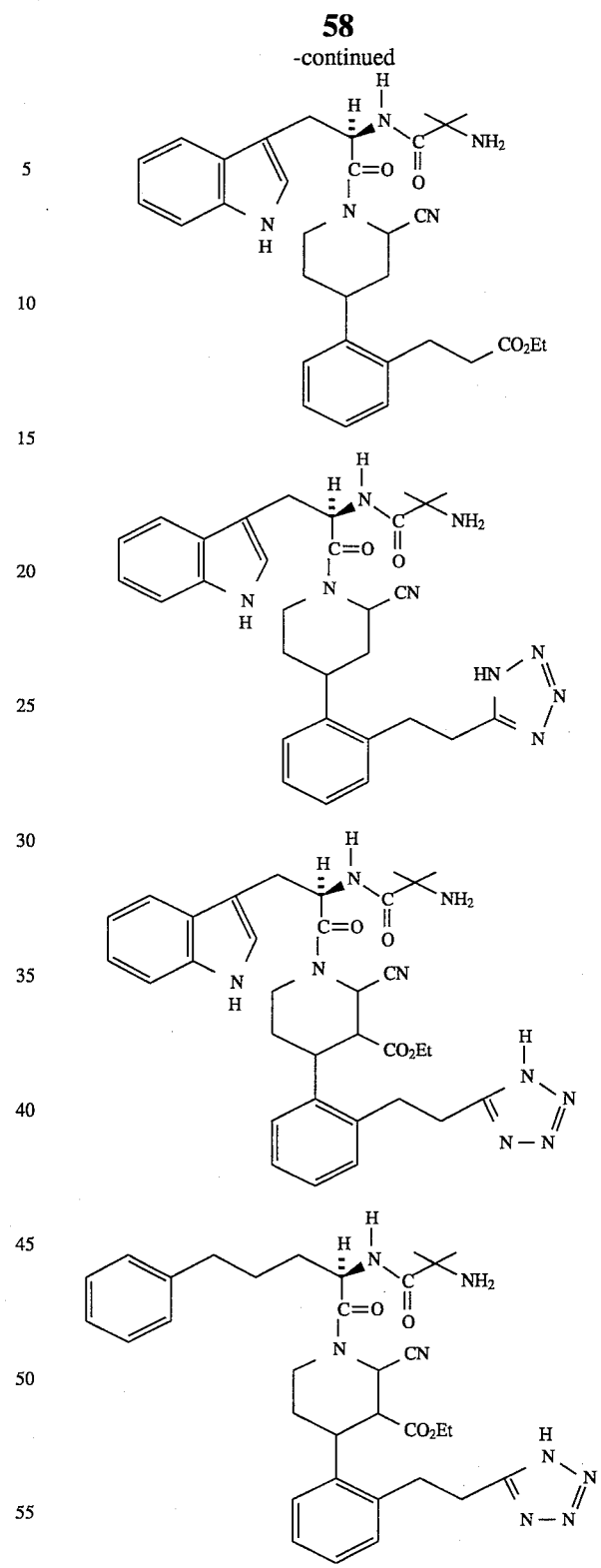

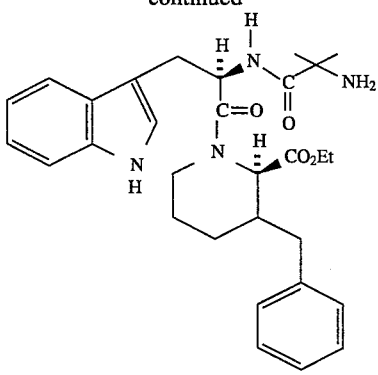

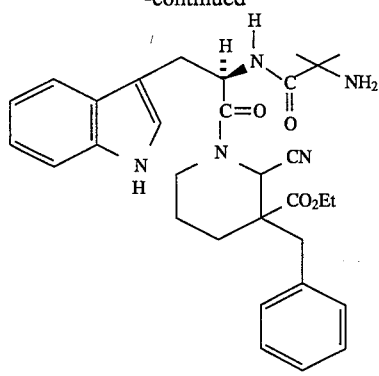

and pharmaceutically acceptable salts and individual diastereomers thereof.

6. A composition useful for increasing the endogenous production or release of growth hormone in a human or an animal which comprises an inert carrier and an effective amount of the compound of claim 1.

7. A method for increasing levels of endogenous growth hormone in a human or an animal which comprises administering to such human or animal an effective amount of the compound of claim 1.

* * * * *